(12) United States Patent
White et al.

(10) Patent No.: US 6,958,401 B2
(45) Date of Patent: *Oct. 25, 2005

(54) METHOD FOR SYNTHESIZING EPOTHILONES AND EPOTHILONE ANALOGS

(75) Inventors: James David White, Philomath, OR (US); Rich Garrett Carter, Oxford, MS (US); Kurt Frederick Sundermann, Corvallis, OR (US)

(73) Assignee: The State of Oregon acting by and through the State Board of Higher Education on behalf of Oregon State University, Corvallis, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/352,340

(22) Filed: Jan. 27, 2003

(65) Prior Publication Data

US 2003/0187273 A1 Oct. 2, 2003

Related U.S. Application Data

(60) Division of application No. 09/846,154, filed on Apr. 30, 2001, now Pat. No. 6,596,875, which is a continuation-in-part of application No. 09/499,596, filed on Feb. 7, 2000, now abandoned.
(60) Provisional application No. 60/118,883, filed on Feb. 5, 1999.

(51) Int. Cl.[7] .................... C07D 277/22; A61P 35/00
(52) U.S. Cl. .................................. 548/203; 548/204
(58) Field of Search ............................ 548/203, 204

(56) References Cited

U.S. PATENT DOCUMENTS

| | | | |
|---|---|---|---|
| 4,551,433 A | 11/1985 | DeBoer | |
| 4,874,748 A | 10/1989 | Katz et al. | |
| 5,063,155 A | 11/1991 | Cox et al. | |
| 5,098,837 A | 3/1992 | Beckmann et al. | |
| 5,149,639 A | 9/1992 | Katz et al. | |
| 5,969,145 A | 10/1999 | Schinzer et al. | |
| 6,043,372 A | 3/2000 | Schinzer et al. | |
| 6,090,601 A | 7/2000 | Gustafsson et al. | |
| 6,302,838 B1 | 10/2001 | O'Reilly et al. | |
| 6,303,342 B1 | 10/2001 | Julien et al. | |
| 6,358,719 B1 | 3/2002 | Schupp et al. | |
| 6,410,301 B1 | 6/2002 | Julien et al. | |
| 6,441,186 B1 * | 8/2002 | Nicolaou et al. ........... | 548/204 |
| 6,723,854 B2 * | 4/2004 | Danishefsky et al. ....... | 548/203 |
| 2002/0058817 A1 | 5/2002 | Danishefsky et al. | |
| 2002/0062030 A1 | 5/2002 | White et al. | |

FOREIGN PATENT DOCUMENTS

| DE | WO 93/10121 | 5/1993 |
|---|---|---|
| DE | WO 97/19086 | 5/1997 |
| DE | WO 98/22461 | 5/1998 |
| DE | WO 98/38192 | 9/1998 |
| DE | WO 98/08849 | 10/1998 |

OTHER PUBLICATIONS

Nicolaou et al., 2002, CAS:137:185358.*
Danishefsky et al., 1999, CAS:130:124934.*
Claims as Pending in U.S. Appl. No. 09/846,154, filed Apr. 30, 2001 (Pub. No. 2002/0062030, published May 23, 2002).
Applicants' copending U.S. Appl. No. 10/354,694, filed Jan. 29, 2003.
Applicants' U.S. Appl. No. 09/499,596, filed Feb. 7, 2000, now abandoned.
Protest Filed Under 37 CFR § 1.291, U.S. Appl. No. 09/846,154, 30 pages. Served on applicants on Feb. 10, 2003.
Rivkin et al. Complex Target–Oriented Total Synthesis in the Drug Discovery Process: The Discovery of a Highly Promising Family of Second Generation Epothilones. *J. Am. Chem. Soc.* 2003, published on the Web Feb. 6, 2003.
White et al. Synthesis, Conformational Analysis, and Bioassay of 9,10–Didehydroepothilone D. *Org. Lett.* 2002, 4, 995–997. Published on the Web Feb. 27, 2002.
White et al. Total Synthesis of Epothilone B, Epothilone D, and *cis*– and *trans*–9,10–Dehydroepothilone D. *J. Am. Chem. Soc.* 2001, 123, 5407–5413.
White et al. Total Synthesis of Epothilone B, Epothilone D, and *cis*– and *trans*–9 ,10–Dehydroepothilone D [*J. Am. Chem. Soc.* 2001, 123, 5407–5413]. ACS Publications Division Home Page. http://pubs.acs.org (accessed Feb. 3, 2003).
Höfle, G.; Bedorf, N.; Gerth, H.; Reichenbach, H. *Chem. Abstr.*, 120, 52841, 1993.

(Continued)

*Primary Examiner*—Kamal A. Saeed
*Assistant Examiner*—Robert Shiao
(74) *Attorney, Agent, or Firm*—Klarquist Sparkman LLP

(57) ABSTRACT

A method for making epothilones and epothilone analogs is described, as are novel compounds made by the method. One embodiment of the method was used to synthesize epothilone B by a convergent approach that entailed Wittig coupling of an ylide derived from phosphonium bromide with an aldehyde. The former was prepared from propargyl alcohol by a nine-step pathway which installed both trisubstituted double bonds with clean Z configuration. Macrolactonization of a resulting seco acid provided the following intermediate diene epothilone analog. Selective saturation of the 9,10-olefin and subsequent epoxidation provided epothilone B.

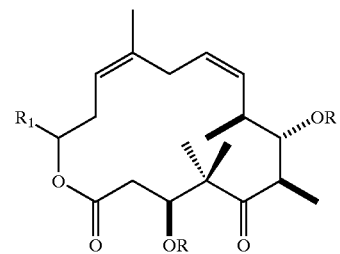

4 Claims, No Drawings

OTHER PUBLICATIONS

Höfle G.; Bedorf, N.; Steinmeth, H.; Schomburg, D.; Gerth. H.; Reichenbach, H. *Angew. Chem. Int. Ed. Engl., 35*, 1567, 1996.
Gerth, K., et al., *Antibiot., 49*, 560–563, 1996.
Kirschner et al., *Cell, 45*, 329–342, 1986.
Mitchison et al., *Nature, 312*, 237–242, 1984.
Toso R. J., *Biochemistry, 32*, 1285–1293, 1993.
Kowalski R. J., et al., *J. Biol. Chem.*, 272, 2534–2541, 1997.
Nicolaou, K.C.; Ninkovic, S.; Sarabia, F.; Vourloumis, D.; He, Y.; Vallberg, H.; Finlay, M.R.V.; Yang, Z. *J. Am. Chem. Soc., 119*, 7974, 1997.
Meng, D.; Bertinato, P.; Balog, A.; Su, D.–S.; Kamenecka, T.; Sorensen, E.J.; Danishefsky, S.J. *J. Am. Chem. Soc., 119*, 10073, 1997.
May, S.A.; Grieco, P. *Chem. Commun.*, 1597, 1998.
Schinzer, D.; Bauer, A.; Schieber, J. *Synlett*, 861, 1998.
White, J.D.; Tiller, T.; Ohba, Y.; Porter, W.J.; Jackson, R.W.; Wang, S.; Hanselmann, R.; *Chem. Commun., 79*, 1998.
Mulzer, J.; Mantoulidis, A. *Tetrahedron Lett., 37*, 9179, 1996.
Claus, E.; Pahl, A.; Jones, P.G.; Meyer, H.M.; Kalesse, M. *Tetrahedron Lett., 38*, 1359, 1997.
Gabriel, T.; Wessjohann, L. *Tetrahedron Lett., 38*, 1363, 1997.
Taylor, R.E.; Haley, J.D. *Tetrahedron Lett., 38*, 2061, 1997.
De Brabander, J.D.; Rosset, S.; Bernardinelli, G. *Synlett*, 824, 1997.
Chakraborty, J.K.; Dutta, S. *Tetrahedron Lett., 39*, 101, 1998.
Liu, Z.–Y.; Yu, C.–Z.; Yang, J.D. *Synlett*, 1383, 1997.
Liu, Z.–Y.; Yu, C.–Z; Wang, R.–F.; Li, G. *Tetrahedron Lett., 39*, 5261, 1998.
Mulzer, J.; Mantoulidis, A.; Öhler, E. *Tetrahedron Lett., 38*, 7725, 1997.
Bijoy, P.; Avery, M.A. *Tetrahedron Lett. 39*, 209, 1998.
Su et al., *Angew. Chem. Int. Ed. Engl., 36*, 757, 1997.
Gilbert et al., *J. Org. Chem., 47*, 1837, 1982.
Inanaga et al., *Bull Chem. Soc. Jpn.*, 1979, 52, 1989.
Müller et al., *Synlett*, p. 521, 1996.
Farina and Krishnan, *J. Am. Chem. Soc., 113*, 9585, 1991.
Balog et al., *Angew. Chem. Int Ed. Engl, 35*, 2801, 1996.
Nicolaou et al., *Angew. Chem. Int Ed. Engl, 35*, 2399, 1996.
Nicolaou et al., *Angew. Chem. Int Ed. Engl., 36*, 2097, 1997.
Nicolaou et al., *Angew. Chem. Int Ed. Engl., 37*, 2015, 1998.

* cited by examiner

METHOD FOR SYNTHESIZING EPOTHILONES AND EPOTHILONE ANALOGS

CROSS REFERENCE TO RELATED APPLICATION

This application is a divisional application of application Ser. No. 09/846,154, filed on Apr. 30, 2001, now is U.S. Pat. No. 6,596,875, which is a continuation-in-part of application Ser. No. 09/499,596, filed on Feb. 7, 2000, now abandoned which claims benefit of 60/118,883, filed on Feb. 5, 1999.

ACKNOWLEDGEMENT OF GOVERNMENT SUPPORT

The United States government may have certain rights in this technology pursuant to Grant No. GM-50574, awarded by the National Institutes of Health.

FIELD

The present invention concerns a method for making epothilones and epothilone analogs, and compounds made by the method.

BACKGROUND

I. Introduction

Epothilones A (2) and B (4) were discovered by Höfle and coworkers while examining metabolites of the cellulose-degrading myxobacterium *Sorangium cellulosum* (Myxococcales) as potential antifungal agents. Höfle, G.; Bedorf, N.; Gerth, H.; Reichenbach (GBF), DE-B 4138042, 1993 (*Chem. Abstr.* 1993, 120, 52841). Höfle, G.; Bedorf, N.; Steinmeth, H.; Schomburg, D.; Gerth. H.; Reichenbach, H. *Angew. Chem. Int. Ed. Engl.* 1996, 35, 1567.

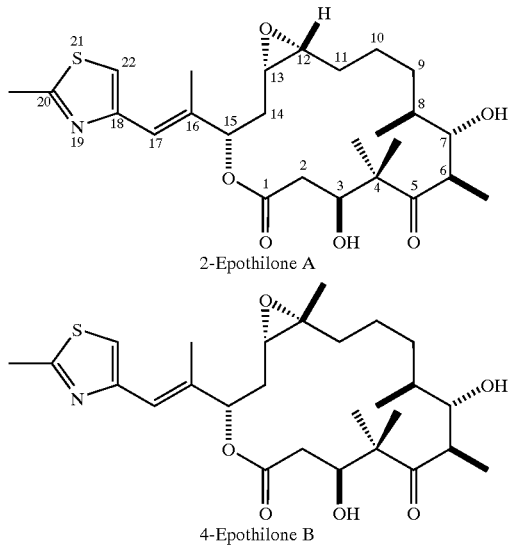

Initial investigations by scientists at the Gesellschaft für Biotechnologische Forschung in Germany concerned the action of epothilones against fungi, bacteria, and a variety of animal cell lines. Höfle, G. et al., *Chem. Abstr.*, 1993, 120, 52841. The epothilones tested had only a narrow spectrum of antifungal activity, but had a rather dramatic effect against oomycetes, such as *Phytophotora infestans*, the causative species of potato-blight disease. Nicolaou, K. C. et al., "Chemical Biology of Epothilones," *Angew. Chem. Int. Ed.*, 1998, 37, 2015, which is incorporated herein by reference.

Although the antifungal spectrum of 2 and 4 proved to be quite narrow, scientists at Merck found that these macrolides are highly cytotoxic. Bollag, D. M.; McQueney, P. A.; Zhu, J.; Hensens, O.; Koupal, L.; Liesch, J.; Goetz, M.; Lazarides, E.; Woods, C. M. *Cancer Res.* 1995, 55, 2325. The epothilones had powerful activity against mouse fibroblast and leukemia cells (2 ng $mL^{-1}$) and strong immunosuppressive activity. Gerth, K., et al., *Antibiot.,* 1996, 49, 560–563. By observing the effect of the epothilones on induction of tubulin polymerization to microtubules and noting that 2 and 4 are competitive inhibitors of Taxol with almost identical $IC_{50}$ values, it was concluded that epothilones act at the cellular level by a mechanism similar to Taxol. Bollag, D. M. *Exp. Opin. Invest. Drugs* 1997, 6, 867; Nicolaou, et al., *Angew. Chem. Int. Ed. Engl.*, supra. Epothilone B (2) was particularly impressive in these assays, having a 2,000–5,000-fold higher potency than Taxol in multiple-drug-resistant cell lines. Bollag, D. M.; et al., *Cancer Res.* 1995, supra.

After scientists from Merck reported their findings on the mode of action of epothilones in 1995, interest in these compounds increased. The Merck scientists subjected tens-of-thousands of compounds to biological assays for Taxol-like tubulin-polymerization activity. Their only hits were epothilones A and B.

II. Tubulin and Microtubules

Tubulin polymerization-depolymerization plays an important role in the cell cycle, particularly during mitosis. Tubulin is a heterodimer protein comprising globular$\alpha,\beta$-tubulin subunits. Tubulin is the monomeric building block of microtubules. Microtubules are one of the fundamental structural components of the cytoskeleton in all eukaryotic cells. Microtubules help develop and maintain the shape and structure of the cell as needed. They may operate alone, or in conjunction with other proteins to form more complex structures, such as cilia, centrioles, or flagella. Nicolaou et al., at 2019, supra.

Structurally, microtubules are regular, internetworked linear polymers (protofilaments) of highly dynamic assemblies of heterodimers of $\alpha$ and $\beta$ tubulin. Nicolaou et al., supra. When thirteen of these protofilaments are arranged parallel to a cylindrical axis they selfassemble to form microtubes. These polymers form tubes of approximately 24 nm in diameter and up to several $\mu$m in length. Nicolaou et al., supra.

The growth and dissolution of microtubules are regulated by bound GTP molecules. During polymerization, GTP molecules hydrolyze to guanosine diphosphate (GDP) and orthophosphate (Pi). The half-life of tubulin at 37° C. is nearly a full day, but that of a given microtubule may be only 10 minutes. Consequently, microtubules are in a constant state of flux to respond to the needs of the cell. Microtubule growth is promoted in a dividing or moving cell, but is more controlled in a stable, polarized cell. The regulatory control is exerted by adding (for growth) or hydrolyzing (for shrinkage) GTP on the ends of the microtubule.

Microtubules are major components of the cellular apparatus and play a crucial role in mitosis, the process during cell replication in which the duplicated genetic material in the form of chromosomes is partitioned equally between two daughter cells. When cells enter mitosis, the cytoskeletal microtubule network (mitotic spindle) is dismantled by melting at the center, and two dipolar, spindle-shaped arrays of microtubules are formed outwards from the centrosome. Nicolaou et al., at 2020, supra. In vertebrate cells, the centrosome is the primary site of microtubule nucleation (microtubule-organizing center or MTOC). At metaphase, the dynamic action of the microtubules assembles the chromosomes into an equatorial position on the mitotic spindle. At anaphase, the microtubule dynamics change and the chromosomes partition and move to the new spindle poles on the dynamic microtubules, where the new cells are being formed. Nicolaou et al., supra. By this process, the parent cell duplicates its chromosomes, which provides each of the two daughter cells with a complete set of genes. When it is time for a eukaryotic cell to divide, microtubules pull its chromosomes apart and pushes them into the two emerging daughter cells. The rate at which microtubules change their length increases by 20- to 100-fold during mitosis relative to the rate during interphase. These rapid dynamics are sensitive to tubulin-interactive agents which exert their antimitotic action at the metaphase-to-anaphase transition. Kirschner et al., Cell, 1986, 45, 329–342.

III. Anticancer Drugs that Disrupt Microtubule Dynamics

A number of anticancer drugs having diverse molecular structures are cytotoxic because they disrupt microtubule dynamics. Most of these compounds, including known chemotherapeutic agents colchicine, colcemid, podophyllotoxin, vinblastine, and vincristine, interfere with the formation and growth of microtubules and prevent the polymerization of microtubules by diverting tubulin into other aggregates. This inhibits cell proliferation at mitosis.

Vinblastine binds to the ends of microtubules. Vinblastine's potent cytotoxicity appears to be due to a relatively small number of end-binding molecules. Mitchison et al., Nature, 1984, 312, 237–242.

Colchicine first binds to free tubulin to form complexes. These complexes are incorporated into the microtubules at the growth ends in relatively low concentrations, but show profound effects on the microtubule dynamics. Toso R. J., Biochemistry, 1993, 32, 1285–129.

Taxol disturbs the polymerization-depolymerization dynamics of microtubules in vitro, by binding to the polymeric microtubules and stabilizing them against depolymerization. Cell death is the net result. Epothilones appear to act by the same mechanism and bind to the same general regions as Taxol does. Bollag et al., Cancer Res., 1995, 55, 2325–2333. Epothilones displace Taxol from its receptor, but bind in a slightly different manner to microtubules, as suggested by their action against Taxol-resistant tumor cells, which contain mutated tubulin. Each tubulin molecule of the microtubules contains a Taxol binding site. Taxol and epothilone binding markedly reduce the rate of $\alpha/\beta$ tubulin dissociation.

Merck scientists compared the effects of the epothilones and Taxol on tubulin and microtubules and reported higher potencies for both epothilones A and B as tubulin polymerization agents (epothilone B>epothilone A>Taxol). All three compounds compete for the same binding site within their target protein. The epothilones exhibit similar kinetics in their induction of tubulin polymerization, and gave rise to microscopic pictures of stabilized microtubules and damaged cells that were essentially identical to those obtained with Taxol. Epothilones are superior to Taxol as killers of tumor cells, particularly multiple drug resistant (MDR) cell lines, including a number resistant to Taxol. In some of the cytotoxicity experiments, epothilone B demonstrated a 2,000–5,000-fold higher potency than Taxol, as stated above. Moreover, in vivo experiments, carried out recently at Sloan Kettering in New York involving subcutaneous implantations of tumor tissues in mice, proved the superiority of epothilone B.

On treatment with epothilones B, cells appear to be in disarray with their nuclei fragmented in irregular shapes and the tubulin aggregated in distinct wedge-shaped bundles. By interacting with tubulin, the epothilones block nuclear division and kill the cell by initiating apoptosis.

Recently, Hamel and co-workers examined the actions of epothilones A and B with additional colon and ovarian carcinoma cell lines and compared them with the action of Taxol. Kowalski R. J., et al., J. Biol. Chem., 1997, 272, 2534–2541. Pgp-overexpressing MDR colon carcinoma lines SW620 and Taxol-resistant ovarian tumor cell line KBV-1 retained susceptibility to the epothilones. With Potorous tridactylis kidney epithelial (PtK2) cells, examined by indirect immunoflourescence, epothilone B proved to be the most active, inducing extensive formation of microtubule bundles. Nicolaou et al., at 2022, supra.

Epothilone A initiates apoptosis in neuroblastoma cells just as Taxol does. Unlike Taxol, epothilone A is active against a Pgp-expressing MDR neuroblastoma cell line (SK-N SH). And, the efficacy of epothilone was not diminished despite the increase of the Pgp level during administration of the drug.

IV. Taxol Side Effects

Taxol molecules bind to microtubules, making cell division impossible, which kills the cells as they begin to divide. Since cancer cells divide more frequently than healthy cells, Taxol damages tumors where runaway cell division occurs most profoundly. Other rapidly dividing cells, such as white blood cells and hair cells, also can be attacked. Consequently, side effects are experienced by patients taking the drug. Chemotherapy with Taxol frequently is accompanied by immune system suppression, deadening of sensory nerves, nausea, and hair loss (neutropenia, peripheral neuropathy, and alopecia).

Taxol exhibits endotoxin-like properties by activating macrophages, which in turn synthesize proinflammatory cytokines and nitric oxide. Epothilone B, despite its similarities to Taxol in its effects on microtubules, lacked any IFN-γ-treated murine-macrophage stimulatory activity as measured by nitric oxide release, nor did it inhibit nitric oxide production. Epothilone-mediated microtubule stabilization does not trigger endotoxin-signaling pathways, which may translate in clinical advantages for the epothilones over Taxol in terms of side effects.

The importance of the epothilones as therapeutic agents recently was discussed on the front page of the Jan. 27, 2,000 edition of the Wall Street Journal. This article states:

But Taxol has its drawbacks. Some fast-dividing cancer cells can mutate into forms resistant to the drug. Often, patients with advanced cancer who respond at first to Taxol don't respond after several cycles of treatment because their cells become resistant, too. Despite conducting dozens of trials over the years, Bristol-Myers has been frustrated in its efforts to expand Taxol's effectiveness beyond certain breast, ovarian and lung cancers.

That's why the new drugs, broadly classified as part of a family of chemicals known as the epothilones, hold such promise. In studies not yet published, Bristol-Myers and others have shown that the epothilones disrupt cell division through the same biochemical pathway as Taxol. But for reasons scientists are only beginning to understand, the new drugs are equally effective against cancer cells already resistant to Taxol, as well as cells that develop resistance over time.

V. Syntheses of Epothilones

Based on the biological activity of the epothilones and their potential as antineoplastics, it will be apparent that there is a need for an efficient method for making epothilones and epothilone analogs. Four total syntheses of 4, and several incomplete approaches, are known. See, for example: (1) Nicolaou, K. C.; Ninkovic, S.; Sarabia, F.; Vourloumis, D.; He, Y.; Vallberg, H.; Finlay, M. R. V.; Yang, Z. J. Am. Chem. Soc. 1997, 119, 7974; (2) Meng, D.; Bertinato, P.; Balog, A.; Su, D. -S.; Kamenecka, T.; Sorensen, E. J.; Danishefsky, S. J. J. Am. Chem. Soc. 1997, 119, 10073; (3) May, S. A.; Grieco, P. Chem. Commun. 1998, 1597; (4) Schinzer, D.; Bauer, A.; Schieber, J. Synlett 1998, 861; (5) Mulzer, J.; Mantoulidis, A. Tetrahedron Lett. 1996, 37, 9179; (6) Claus, E.; Pahl, A.; Jones, P. G.; Meyer, H. M.; Kalesse, M. Tetrahedron Lett. 1997, 38, 1359; (7) Gabriel, T.; Wessjohann, L. Tetrahedron Lett. 1997, 38, 1363; (8) Taylor, R. E.; Haley, J. D. Tetrahedron Lett. 1997, 38, 2061; (9) Brabander, J. D.; Rosset, S.; Bernardinelli, G. Synlett 1997, 824; (10) Chakraborty, J. K.; Dutta, S. Tetrahedron Lett. 1998, 39, 101; (11) Liu, Z. -Y.; Yu, C. -Z.; Yang, J. D. Synlett 1997, 1383; (12) Liu, Z. -Y.; Yu, C. -Z; Wang, R. -F.; Li, G. Tetrahedron Lett. 1998,39, 5261; (13) Mulzer, J.; Mantoulidis, A.; Öhler, E. Tetrahedron Lett. 1997, 38, 7725; and (13) Bijoy, P.; Avery, M. A. Tetrahedron Lett. 1998, 39 1209.

Methods for making epothilone and epothilone analogs also have been described in the patent literature, including: (1) Schinzer et al., WO 98/08849, entitled "Method for Producing Epothilones, and Intermediate Products Obtained During the Production Process"; and (2) Reichanbach et al., WO 98/22461, entitled "Epothilone C, D, E, and F, Production Process, and Their Use as Cytostatic as well as Phytosanitary Agents." One disadvantage associated with these prior processes for synthesizing epothilones is the lack of stereoselectivity in the production of the Z trisubstituted bond of the desepoxyepothilone. As a result, a new synthetic approach to epothilones and epothilone analogs is required which addresses this and other problems associated with syntheses of the epothilones known prior to the present invention.

SUMMARY

The present invention provides a novel method for making epothilones and epothilone analogs. The method can provide almost complete stereoselectivity with respect to producing the Z trisubstituted double bond of the desepoxyepothilone, and therefore addresses one of the disadvantages associated with methods known prior to the present invention.

One embodiment of the method comprises first providing a compound having Formula 1.

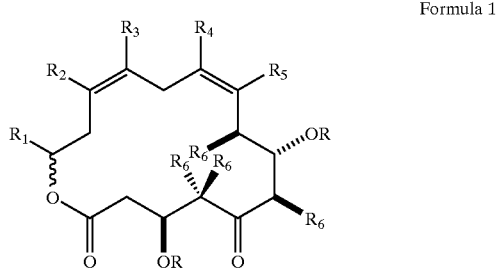

Formula 1

With reference to Formula, 1 R is H or a protecting group, $R_1$ is an aryl group, such as, without limitation, benzene derivatives or the thiazole of epothilone B, $R_2$–$R_5$ substituents independently are selected from the group consisting of H and lower alkyl groups; and $R_6$ substituents independently are selected from the group consisting of lower alkyl groups.

Compounds having Formula 1 are then converted into an epothilone or an epothilone analog. For example, in the synthesis of epothilone B the step of converting the compound can involve first removing the protecting groups, and thereafter forming an epoxide at C-12, C-13.

In preferred embodiments, $R_1$ is the thiazole shown below.

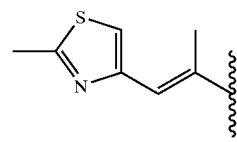

Most known epothilones have this thiazole as the aryl group.

Providing compounds having Formula 1 can be accomplished in a number of ways. One embodiment comprises coupling a first compound having Formula 2,

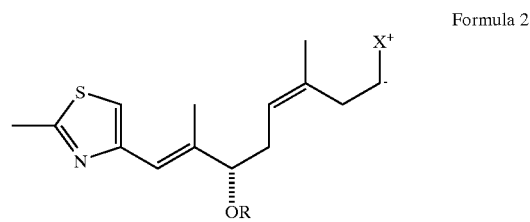

Formula 2 where R is H or a protecting group and X is a functional group or chemical moiety equivalent to a carbanion at a terminal carbon of the first compound, with a second compound having Formula 3

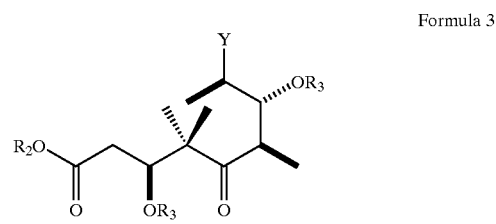

Formula 3

With reference to Formula 3, $R_2$ is H or lower alkyl, $R_3$ is H or a protecting group, and Y is an electrophillic group capable of reacting with and coupling to the terminal carbon of the first compound. The precursor compound is then converted into compounds having Formula 1. For example, two compounds, one having Formula 2 and the other Formula 3, can be coupled by a Wittig reaction where X is $PPH_3^+$ and Y is a carbonyl compound, such as an aldehyde.

Compounds having Formula 1 can be provided by a second embodiment of the present invention. This second embodiment involves coupling a first compound having Formula 4

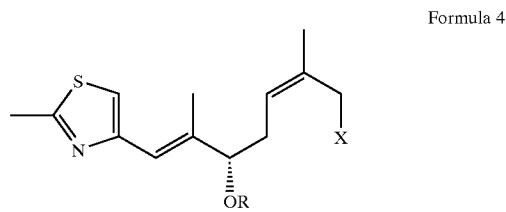

Formula 4 where R is H or a protecting group and X is a halide, with a second alkyne compound having Formula 5

Formula 5

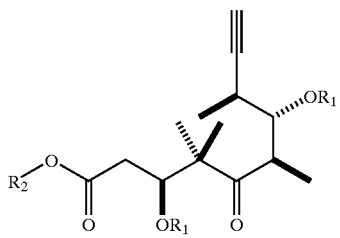

where $R_1$ is H or a protecting group and $R_2$ is H or lower alkyl. This compound is then converted into a compound having Formula 1. This second embodiment can proceed by first forming an enyne precursor compound having Formula 6

Formula 6

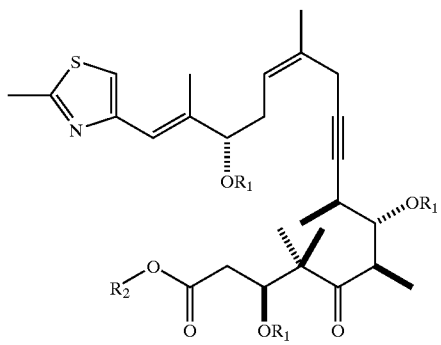

where the substituents are as stated above.

Still another embodiment of the method of the present invention for forming epothilones or epothilone analogs comprises forming the precursor enyne compound having Formula 6 where $R_1$ is H or a protecting group, or a triene compound having Formula 7

Formula 7

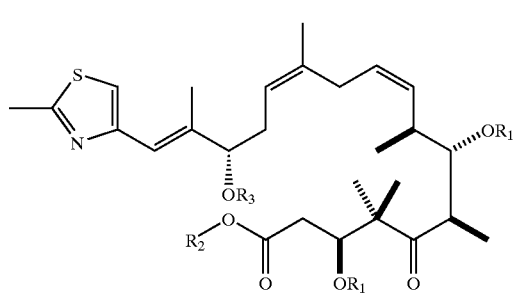

where $R_1$ is H or a protecting group, $R_2$ is H or lower alkyl, and $R_3$ is H or a protecting group. Compounds having Formulas 6 and/or 7 are then converted into a compound having Formula 8, where the carbon atom numbers correspond to the numbering system stated for epothilone A.

Formula 8

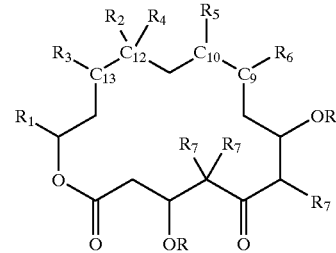

With reference to Formula 8, $R-R_7$ are independently selected from the group consisting of H, lower aliphatic groups, particularly lower alkyl groups, protecting groups, or are bonded to an O in an epoxide or an aziridine. More particularly, R substituents independently are H, lower alkyl, or a protecting group; $R_1$ is an aryl group; $R_2$ is H or lower alkyl; $C_{13}$ and $C_{12}$ are carbons bonded together by a single bond or a double bond; $R_3$ and $R_4$ independently are H, lower aliphatic groups, or are bonded to O in an epoxide or to N in an aziridine; $C_{10}$ and $C_9$ are carbons in a double bond or triple bond, and, where $C_{10}$ and $C_9$ are carbons in a double bond, $R_5$ and $R_6$ independently are H, or lower aliphatic; and $R_7$ substituents independently are selected from the group consisting of lower aliphatic groups. The configuration of the double bond between $C_{10}$ and $C_9$ may be cis or trans or E or Z. Compounds having Formula 8 are then converted into an epothilone or an epothilone analog. Moreover, the compound having Formula 6 may be converted into the compound having Formula 7, such as by catalytic semi-hydrogenation. Lindlar's catalyst has proven an effective catalyst for conducting this catalytic semi-hydrogenation.

The method of the present invention differs from other pathways by assembling the macrolide from two segments, which first are connected at C-9, C-10 before macrolactonization. With reference to the first embodiment of the present invention, fragments were constructed around a preformed Z trisubstituted alkene to circumvent stereochemical problems afflicting known synthetic methods. The 9,10 olefin produced by coupling the two segments confers rigidity on the one portion of the epothilone macrocycle that exhibits flexibility, and hence may be expected to impact its tubulin binding properties. Moreover, this alkene provides a chemical moiety from which novel epothilone analogues can be prepared.

Epothilones, such as epothilone A, epothilone B, epothilone C, epothilone D, epothilone E, and epothilone F, can be made by the method of the present invention. The present invention also provides novel compounds that can be made by the method. These compounds typically have Formula 8

Formula 8

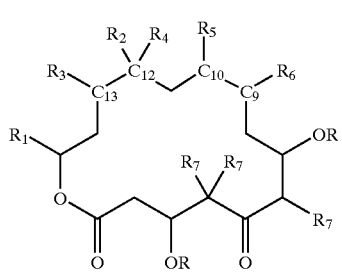

where the substituents are as described above. Preferred compounds satisfying Formula 8 include one or more of the following: (1) R being hydrogen; (2) $R_1$ being the aryl thiazole side chain of the epothilones; (3) $R_2$ being hydrogen or methyl; (4) $R_3$–$R_6$ being hydrogen or methyl, or $R_3$ and $R_4$ and/or $R_5$ and $R_6$ being bonded to oxygen in an epoxide; (5) $R_7$ being methyl.

Compounds having Formula 8 include several chiral centers, which allows for a plurality of diastereomers. The present invention is directed to all such stereoisomers. But, the epothilones have known stereochemistries at each of the chiral centers. As a result, preferred compounds of the present invention have the same stereochemistries at each chiral center as do the epothilones. This is illustrated below in Formula 9, which shows the stereochemistries of preferred epothilone analogs at each chiral center.

Formula 9

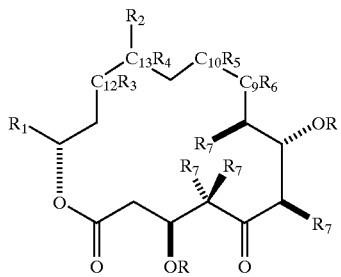

DETAILED DESCRIPTION

The process of the present invention can be used to make known epothilones A, B, C, D, E and F, as well as analogs of these compounds, including the cryptothilones, which typically are dilactone or lactone-amide-type analogs of the epothilones. The cryptothilones are hybrid structures which include a portion of cryptophycins and a portion of the epothilones. One such novel diene analog 10 has double bonds at positions C-9, C-10, and C-12, C-13, including all combinations of cis (10) and trans (11) (Z and E) double bonds

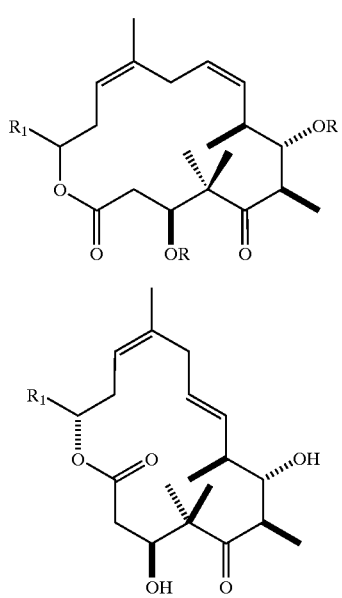

Using compound 10 and/or 11 to make analogs of epothilones, such as the cryptothilones, provides advantages relative to prior known syntheses, as indicated above.

A method for making diene 10 and converting 10 into, for example, epothilone B, as well as other epothilones and epothilone analogs, is described below.

I. Epothilone Structures and Epothilone Analogs

Formula 8 is a generic structural formula for diene and enyne derivatives of Compound 10.

Formula 8

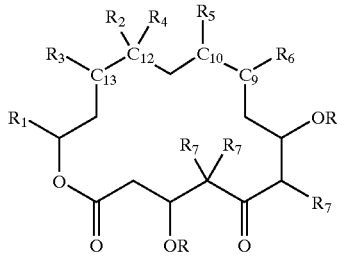

Preferred compounds have the stereochemistries shown in Formula 9.

Formula 9

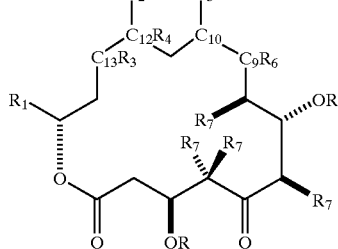

With reference to Formulas 8 and 8, R is H, lower aliphatic, preferably lower alkyl, or a protecting group; $R_1$ is an aryl group; $C_{13}$ and $C_{12}$ are carbons bonded together by a single or double bond; $R_3$ and $R_4$ independently are H, lower alkyl, or are bonded to oxygen in an epoxide or to nitrogen in an aziridine; $C_{10}$ and $C_9$ are carbons in a single bond, double bond or triple bond, with preferred compounds having $C_{10}$ and $C_9$ bonded together by a double bond or a triple bond; if $C_{10}$ and $C_9$ are bonded together by a double bond, the configuration of the double bond may be cis or trans or E or Z; and $R_5$ and $R_6$ independently are H, lower aliphatic, preferably lower alkyl, or are bonded to heteroatoms in cyclic structures, such as to oxygen in an epoxide or to nitrogen in an aziridine.

As used herein, "lower" refers to carbon chains having 10 or fewer carbon atoms, typically less than 5 carbon atoms. "Lower aliphatic" includes carbon chains having: (a) sites of unsaturation, e.g., alkenyl and alkynyl structures; (b) non-carbon atoms, particularly heteroatoms, such as oxygen and nitrogen; and (c) all branched-chain derivatives and stereoisomers.

The phrase "protecting group" is known to those of ordinary skill in the art of chemical synthesis. "Protecting group" refers generally to a chemical compound that easily and efficiently couples to a functional group, and can be easily and efficiently removed to regenerate the original functional group. By coupling a protecting group to a first functional group of a compound other functional groups can undergo chemical or stereochemical transformation without affecting the chemistry and/or stereochemistry of the first functional group. Many protecting groups are known and most are designed to be coupled to only one or a limited number of functional groups, or are used for particular circumstances, such as reaction conditions. Theodora Greene's *Protecting Groups in Organic Syntheses*, (Wilely Science, 1984), and later editions, all of which are incorporated herein by reference, discuss protecting groups commonly used in organic syntheses. Examples of protecting groups used to protect hydroxyl functional groups for the syntheses of epothilones and epothilone analogs include the silyl ethers, such as t-butyl dimethyl silyl (TBDMS) ethers, and tetrahydropyranyl (THP) ethers.

"Aryl" refers to compounds derived from compounds having aromatic properties, such as benzene. "Aryl" as used herein also includes compounds derived from heteroaromatic compounds, such as oxazoles, imidazoles, and thiazoles.

Preferred aryl groups have Formula 10

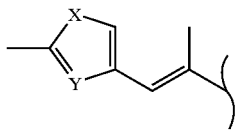

Formula 10 where X and Y are independently selected from the group consisting of heteroatoms, particularly oxygen, nitrogen and sulfur. For the epothilones, and most epothilone analogs, the $R_1$ aryl group is thiazole 18 shown below.

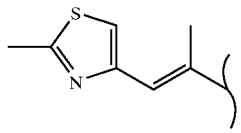

18

$C_{13}$ and $C_{12}$ of Formula 8 are carbons bonded together by a single or double bond. Whether $C_{13}$ and $C_{12}$ are joined by a single or double bond determines, in part, substituents $R_3$ and $R_4$. For example, if $C_{13}$ and $C_{12}$ are coupled by a single bond, then $R_3$ and $R_4$ are selected from the group consisting of hydrogen and lower alkyl. Moreover, if $C_{13}$ and $C_{12}$ are coupled by a single bond then $R_3$ and $R_4$ can be bonded to a heteroatom, such as oxygen and nitrogen, in a cyclic structure, such as an epoxide or an aziridine. Epoxide 20 and aziridine 22 are examples of these compounds.

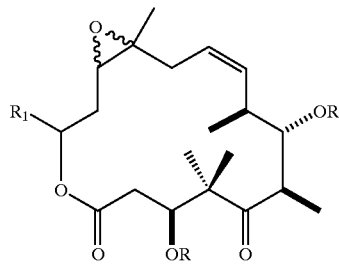

20

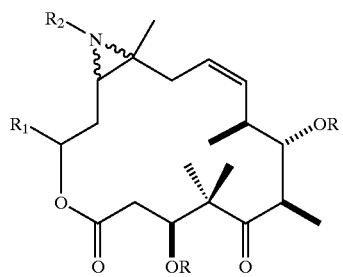

22

Wavy and straight bonds to carbons at chiral centers of these structures indicate that all stereoisomers are within the scope of the present invention. With respect to the aziridine analogs, such as aziridine 22, $R_2$ is selected from the group consisting of hydrogen, lower aliphatic, particularly lower alkyl, acyl, and aryl. Preferred compounds have $R_2$ be hydrogen or lower alkyl.

$C_{10}$ and $C_9$ of Formula 8 are carbons bonded together by a single, double or triple bond. Whether $C_{10}$ and $C_9$ are joined by a single bond, a double bond or a triple bond determines, in part, substituents $R_5$ and $R_6$. For example, if $C_{10}$ and $C_9$ are coupled by a single bond, then $R_5$ and $R_6$ typically are selected from the group consisting of hydrogen and lower aliphatic, preferably lower alkyl. Moreover, if $C_{10}$ and $C_9$ are coupled by a single bond then $R_5$ and $R_6$ also can be bonded to a heteroatom, such as oxygen and nitrogen, in a cyclic structure, such as an epoxide or an aziridine. Epoxide 24 and aziridine 26 provide examples of these compounds.

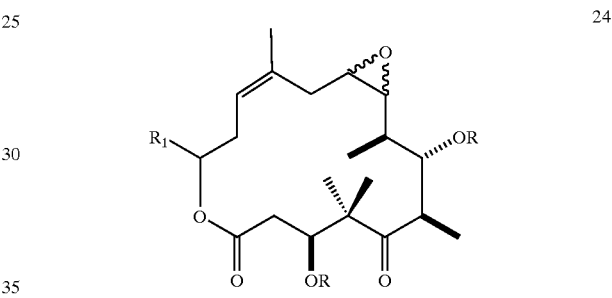

24

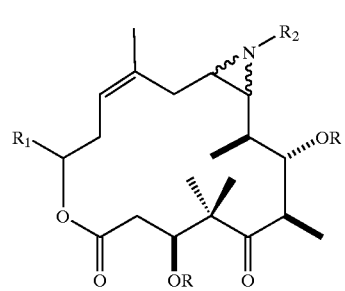

26

Compounds 28, 30, 32 and 34 provide additional examples of epoxide/aziridine epothilone analogs.

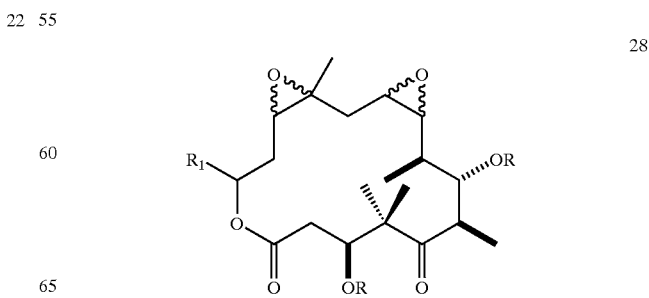

28

-continued

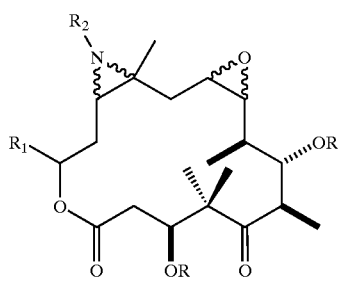

30

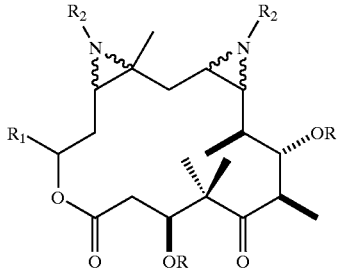

34

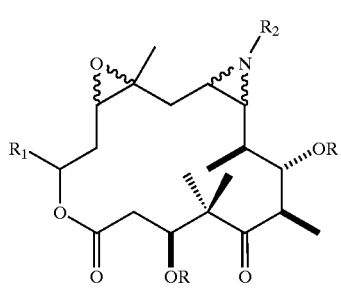

32

II. Biological Activity

Known epothilones have significant biological activity. Novel epothilone analogs made according to the method of the present invention also have been shown to have significant biological activity. For example, Table 1 provides biological data for certain epothilones and epothilone analogs.

TABLE 1

| Compound | Tubulin Poly.[a] | $IC_{50}$ KB-31 (Epidermoid)[b] | $IC_{50}$ KB-8511 (Epidermoid)[b,c] | $IC_{50}$ A549 (lung)[b] | $IC_{50}$ HCT-116 (colon)[b] | $IC_{50}$ PC3-M (prostate)[b] | $IC_{50}$ MCF-7 (breast)[b] |
|---|---|---|---|---|---|---|---|
| 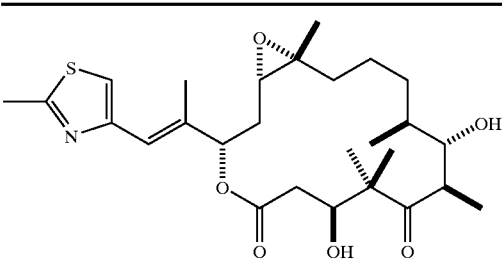 Epothilone B | 95 | 0.17 | 0.16 | 0.16 | 0.34 | 0.32 | 0.29 |
| 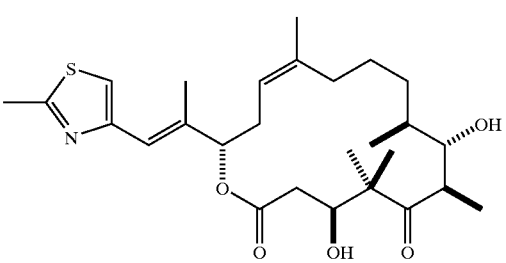 Epothilone D | 88 | 1.94 | 1.00 | 4.62 | 4.48 | 7.40 | 2.31 |
| 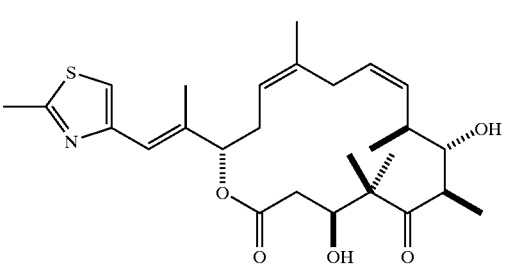 | 56 | 59.39 | 28.54 | 109.03 | 101.83 | 146.47 | 72.00 |

TABLE 1-continued

| Compound | Tubulin Poly.[a] | IC$_{50}$ KB-31 (Epidermoid)[b] | IC$_{50}$ KB-8511 (Epidermoid)[b,c] | IC$_{50}$ A549 (lung)[b] | IC$_{50}$ HCT-116 (colon)[b] | IC$_{50}$ PC3-M (prostate)[b] | IC$_{50}$ MCF-7 (breast)[b] |
|---|---|---|---|---|---|---|---|
| Cis 9,10-Dehydroepothilone D | 36 | 103.70 | 70.37 | 109.27 | 109.97 | 146.80 | 95.03 |
| Trans 9,10-Dehydroepothilone D | | | | | | | |
| Paclitaxel (Taxol) | 53 | 2.67 | 841.80 | 5.19 | 4.88 | 6.62 | 3.26 |

[a]Tubulin polymerization data (induction of porcine tubulin polymerization) are for 5 μM compound concentration relative to the effect of Epothilone B at a concentration of 25 μM, which is defined as 100%.
[b]IC$_{50}$ values are expressed in nM and represent the mean of three independent experiments.
[c]KB8511 is a Pgp-overexpressing sub-line of the KB-31 line.

The antiproliferative activity of cis 9,10-dehydroepothilone D and trans 9,10-dehydroepothilone D was assessed in vitro using a panel of human cancer cell lines. As illustrated in Table 1, cis 9,10-dehydroepothilone was 20- to 30-fold less potent than natural epothilone D, and 330- to 670-fold less potent than epothilone B. Interestingly, trans 9,10-dehydroepothilone D showed biological activity very similar to that of its cis isomer in spite of an apparent difference in the conformation of these two macrolactones. Thus, the average IC$_{50}$ of trans 9,10-dehydroepothilone D for growth inhibition in the cell line panel used in this study was only 1.36-fold higher than that observed for cis 9,10-dehydroepothilone D. As noted for epothilones B and D, cis 9,10-dehydroepothilone D and trans 9,10-dehydroepothilone D retain full anti-proliferative activity against KB-8511 cells, a paclitaxel-resistant cell line overexpressing P-glycoprotein (Table 1). While the tubulin polymerization activity of cis 9,10-dehydroepothilone D and trans 9,10-dehydroepothilone D was lower than of natural epothilone D (56%, 36%, and 88%, respectively) (Table 1), it is conceivable that decreased cellular penetration may contribute to the reduction in antiproliferative potency observed for cis 9,10-dehydroepothilone D and trans 9,10-dehydroepothilone D. The absence of a clear difference in the biological profiles of cis and trans analogues of 9,10-dehydroepothilone D observed here has a parallel in results previously reported for other epothilone analogs. Thus, epothilones incorporating a trans epoxide or trans olefin at C12–C13 have been shown to possess biological activity comparable to their cis isomer.

Taken together, these data support the proposition that the C8–C13 region of the epothilone perimeter is relatively tolerant of structural modification and suggest that the interaction of this segment of the molecule with tubulin is less stringently defined.

III. Method for Making Epothilones

The synthesis of epothilones can be exemplified by a working embodiment of a method for making epothilone B. Epothilone B was synthesized by coupling a first subunit with a second subunit to form a coupled intermediate for forming epothilones. One embodiment of the method comprised coupling a first subunit 36 with a second subunit 38.

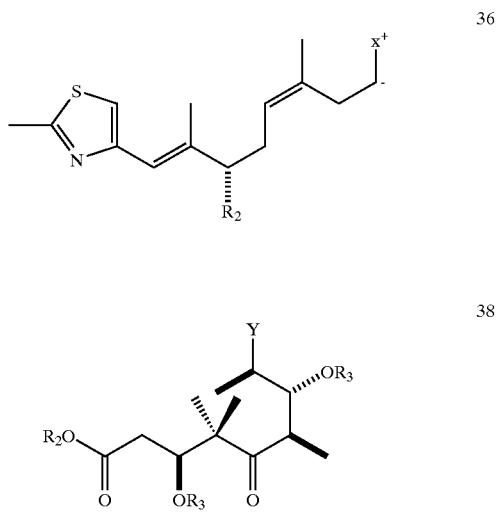

A second embodiment comprised coupling a first allylic halide subunit 40 with a second alkyne subunit 42

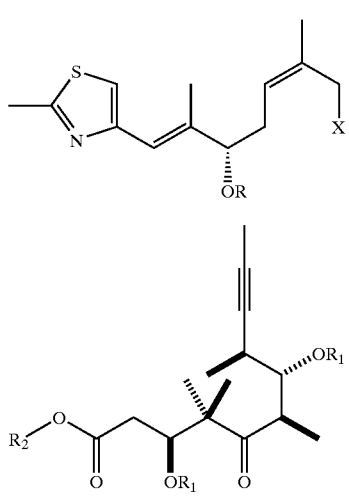

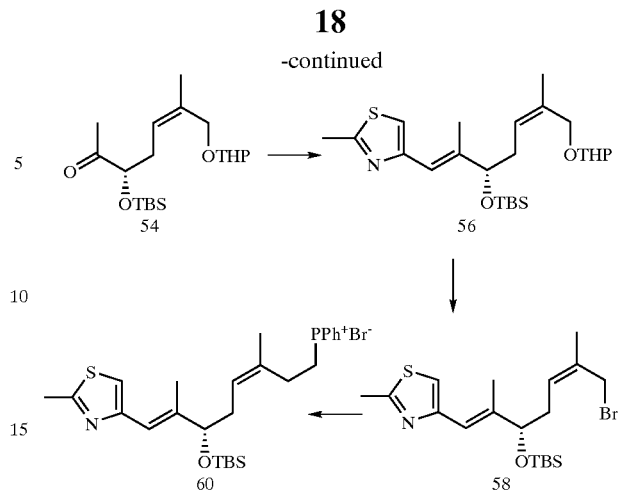

With respect to 36, 38, 40, and 42, the R substituents are as described above.

A first embodiment of a the present method for making epothilones and epothilone analogs comprised making a suitable subunit 36 as illustrated by Scheme 1, i.e., compound 60.

SCHEME 1

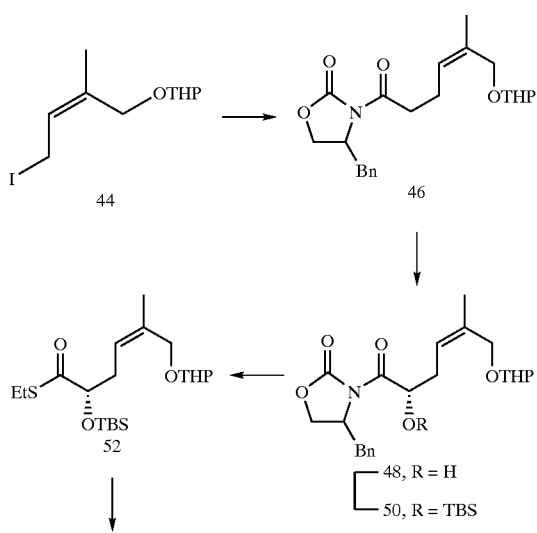

Synthesis of segment 36 began from (Z)-3-iodo-2-methyl-2-propen-1-ol prepared in geometrically pure form from propargyl alcohol. After protection to provide 44, the iodoalkene was converted to the corresponding cuprate, which underwent clean conjugate addition to (S)-3-acryloyl-4-benzyl-2-oxazolidinone (45) to yield 46. Hydroxylation of the sodium enolate derived from 46 with Davis oxaziridine gave 48. (See, for example, Evans et. al., *Chem. Int. Ed Engl.*, Vol. 26, p. 2117, 1997). The configuration of 48 was confirmed by oxidative degradation to dimethyl (S)-malate. Protection of alcohol 48 as silyl ether 50, followed by exposure to catalytic potassium thioethoxide in ethanethiol provided 52, along with recovered oxazolidinone (93%). Treatment of thioester 52 with lithium dimethylcuprate furnished ketone 54, which upon Horner-Emmons condensation with phosphonate 53 (shown below) produced

53

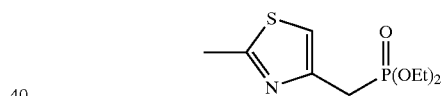

diene 56 in excellent yield, accompanied by 5% of its (Z,Z) isomer. The tetrahydropyranyl ether protecting group was removed using magnesium bromide. The liberated alcohol was converted to bromide 58. Homologation of 58 to phosphonium bromide 60 using triphenylmethylenephosphorane completed the synthesis of segment 36.

One embodiment of a segment 38, i.e., compound 74, was made as shown by Scheme 2.

SCHEME 2

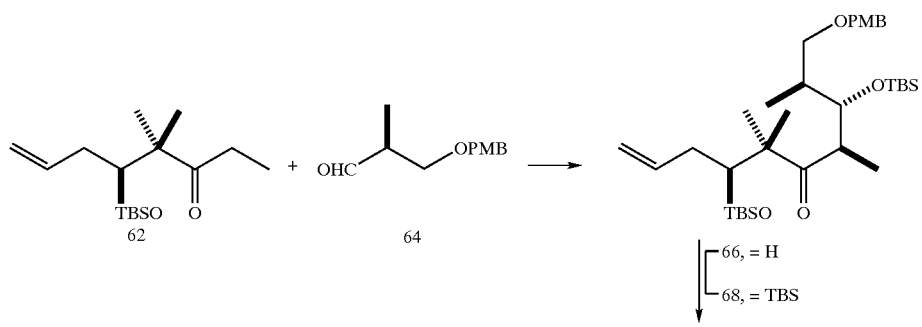

-continued

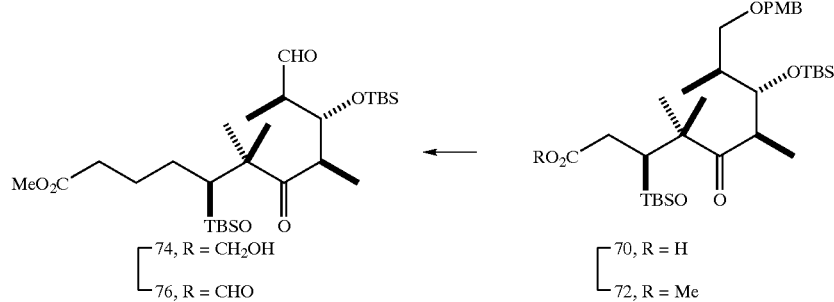

A key construction in one embodiment of a suitable segment 36 involved an aldol condensation of ketone 62 with aldehyde 64. This double stereodifferentiating reaction proceeded in good yield to give anti-Felkin product 66 as the sole stereoisomer. An important contribution to the stereoselectivity of this condensation is made by the p-methoxybenzyl (PMB) ether of 64, since the TBS protected version of this aldehyde resulted only in a 3:2 mixture of 66 and its Felkin diastereomer, respectively. The favorable outcome with 64 is consistent with chelation of the aldehyde carboxyl with both the lithium enolate from 62 and the PMB ether. After protection of 66 as tris ether 68, the terminal olefin was cleaved oxidatively to carboxylic acid 70, which was converted to its methyl ester 72. Hydrogenolysis of the PMB ether and oxidation of the resultant alcohol 74 yielded aldehyde 76.

Subunits 60 and 76 were coupled together, followed by macrolactonization, to provide the diene lactone precursor to epothilone B as shown below in Scheme 3.

SCHEME 3

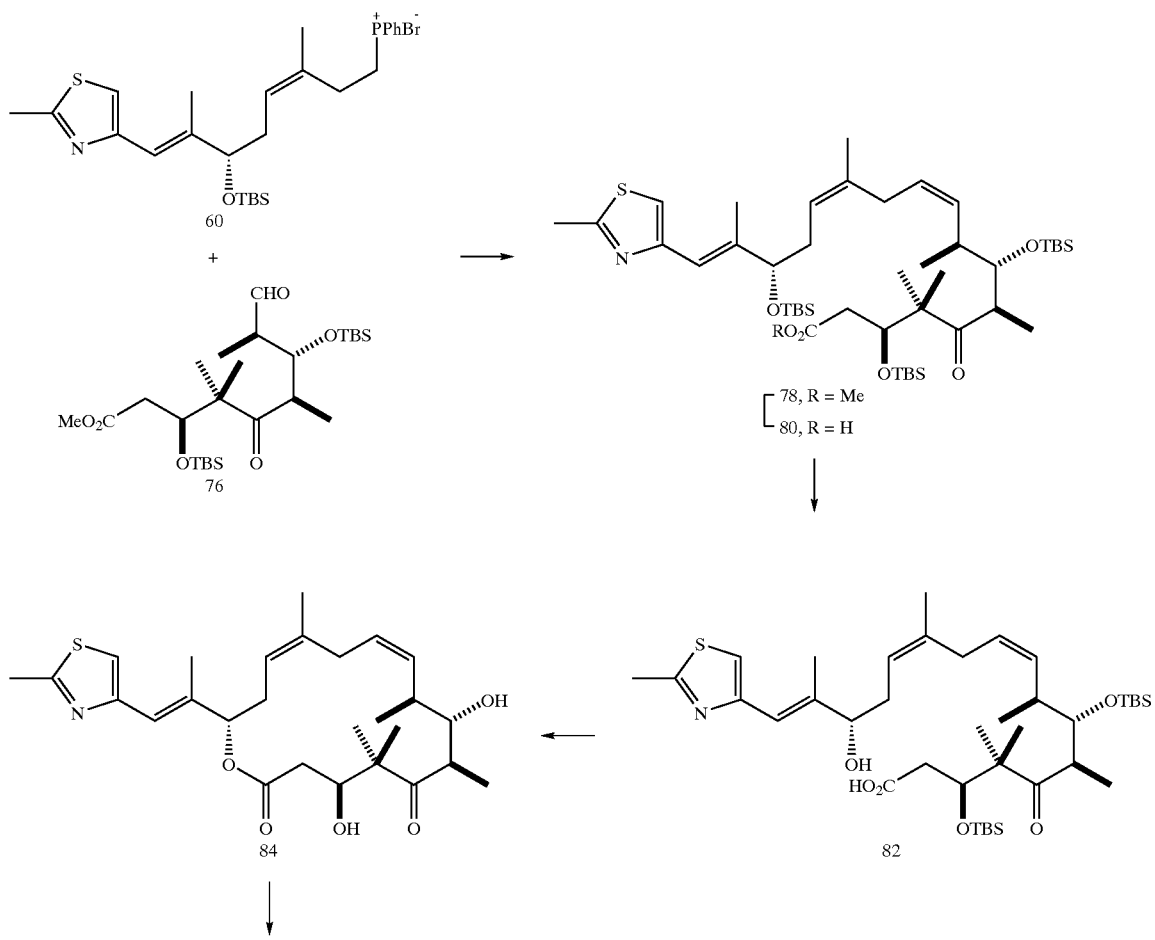

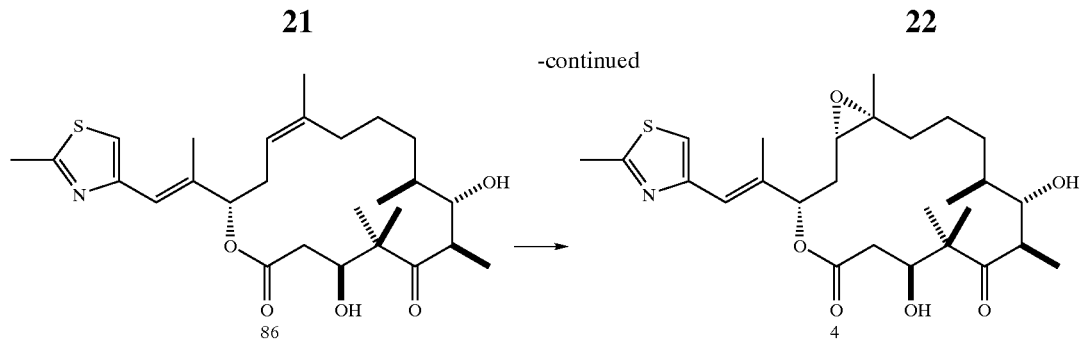

Wittig coupling of the ylide from 58, compound 60, with aldehyde 76 at low temperature afforded triene 78 as a single stereoisomer in excellent yield. Selective removal of the C-15 silyl ether of 78 was unsuccessful. But, after saponification to carboxylic acid 80 this deprotection was readily accomplished with tetra-n-butylammonium fluoride. Macrolactonization of seco acid 82 was carried out under Yamaguchi's conditions and both silyl ethers were cleaved with acid to yield 9,10-dehydrodes-epoxyepothilone B 84.

Compounds made in this manner can be converted to epothilones using conventional chemistry. For example selective hydrogenation of the disubstituted olefin of 84 with diimide gave the known lactone 86. Lactone 86 underwent epoxidation with dimethyldioxirane to produce 4. Epoxidation can be accomplished according to the method of Danishefsky et al., *Angew. Chem.*, 1997, 109, 775; and *Angew. Chem. Int. Ed. Engl.*, 1997, 36, 757, both of which are incorporated herein by reference. Characterization data for both 86 and 4 matched those in the literature and/or of the naturally occurring product. The $^1$H NMR spectrum of 4 was in excellent agreement with that provided by Professor Grieco.

Schemes 1–3 provide a convergent synthesis of epothilone B (2), which generates all seven of its asymmetric centers in a completely stereoselective fashion. In addition, clean Z configuration at the C-12, C-13 double bond is incorporated by this pathway. Finally, the Z olefin at C-9, C-10 provides a chemical moiety from which exploratory structural modifications can be made.

Scheme 4 illustrates a second embodiment of a method for making epothilones and epothilone analogs.

SCHEME 4

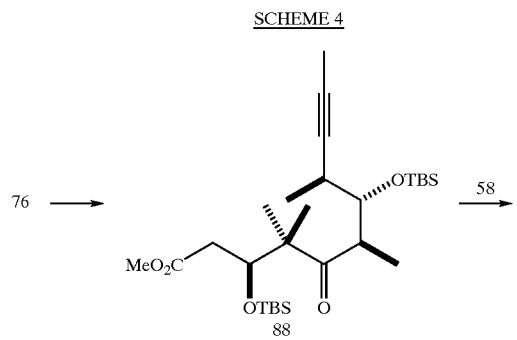

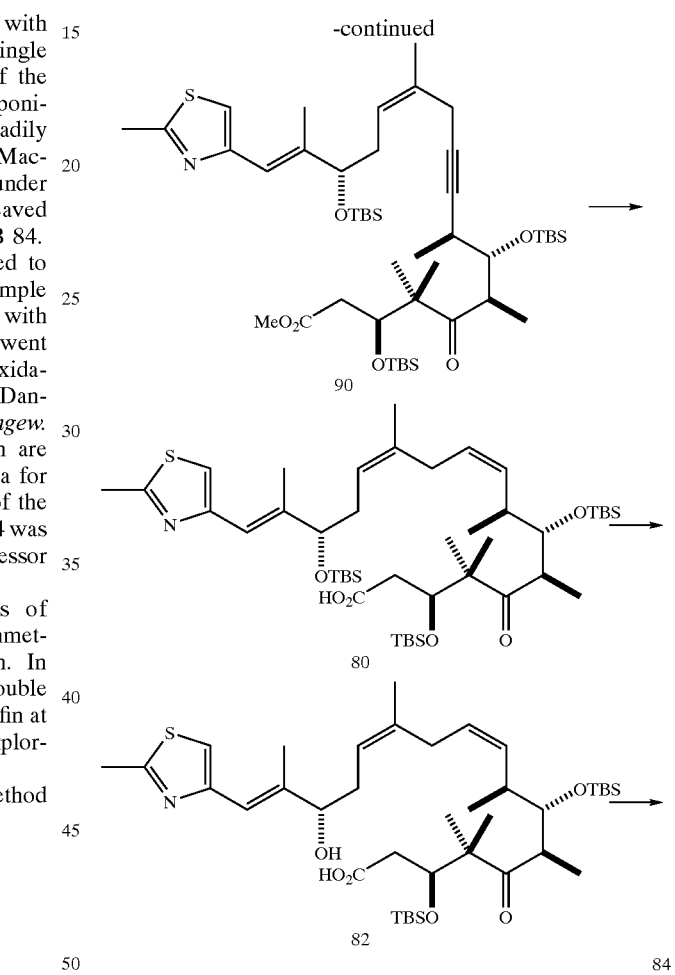

With reference to Scheme 4, compound 76 was made as illustrated above in Scheme 2, and as discussed in more detail in Example 16. Aldehyde 76 was reacted with dimethyl diazophosphonate [J. C. Gilbert et al., *J. Org. Chem.*, 1982, 47, 1837] in THF at −78° C. to provide alkyne 88 in approximately 80% yield. The copper (I) derivative of alkyne 88 was produced and was found to couple with allylic halide 58. This reaction was extensively investigated, and was found to proceed to product 90 best when the conditions for the reaction were as shown in Table 2, using about 5% CuI, Et$_3$N, Et$_2$O-DMF, and about 2.0 equivalents of 88. Conditions investigated for this coupling are summarized below in Table 4.

TABLE 4

| Equivalents of 86 | Coupled With | Reagents/ Conditions | Product Yield |
|---|---|---|---|
| 1.1 | Allylic Halide 56 | 5% CuI, TBAB, K$_2$CO$_3$, DMF | 8 |
| 1.1 | Allylic Halide 56 | 20% CuI, ALIQUOT 336, K$_2$CO$_3$, DMF | 11 |
| 1.1 | Allylic Halide 56 | 50% CuI, Pyrrolidine, DMF | 0 |
| 1.1 | Allylic mesylate of 54 | (a) Ms$_2$O, Et$_3$N, DMF (b) 10% CuI, Na$_2$CO$_3$, TBAB, DMF | 34 |
| 1.1 | Allylic mesylate of 54 | (a) Ms$_2$O, Et$_3$N, CH$_2$Cl$_2$ (b) 20% CuI, Na$_2$CO$_3$, TBAB, DMF | 42 |
| 1.1 | Allylic Halide 56 | 5% CuI, Et$_3$N, Et$_2$O-DMF | 24 |
| 2.0 | Allylic Halide 56 | 5% CuI, Et$_3$N, Et$_2$O-DMF | 60 |

Product 90 was semi-hydrogenated over Lindlar's catalyst [Pd/CaCO$_3$, Pd(OAc)$_2$]. This reaction was found to proceed best when hexanes was used as the solvent. The hydrogenated product was then saponified using NaOH and isopropyl alcohol at 45° C. to provide the corresponding seco acid 80 in approximately 66% yield., The C-15 TBS ether 80 was then deprotected using TBAF and THF by warming the reaction from 0° C. to 25° C., with a yield of about 89%. The selectivity of this reaction is attributed to sterically favorable transilyation involving the carboxylate anion. The resultant silyl ester is hydrolyzed during aqueous work-up. Macrolactonization was then performed under Yamaguchi conditions. Yamaguchi et al., *Bull Chem. Soc. Jpn*, 1970, 52, 1989. The remaining TBS ether protecting groups were then removed using trifluoroacetic acid (TFA) in dichloromethane at 0° C. to provide compound 84. Compound 84 was then converted to 4 as discussed with respect to Scheme 3 and Examples 21, 22 and 23.

Schemes 5, 6, and 7 illustrate an embodiment of a synthesis via Stille coupling that yields epothilone derivatives containing a trans (or E) double bond between C$_9$ and C$_{10}$ (See Formula 8).

With reference to Scheme 5, compound 92 was esterified with 2-(trimethylsilyl)ethanol using Mitsunobu conditions to provide 94. Hydrogenolysis removed the p-methoxybenzyl ether from 94, and oxidation of alcohol 96 afforded an aldehyde which was reacted with Bestmann's reagent (Müller et al., *Synlett*, p. 521, 1996) to give terminal alkyne 96. Hydrostannylation of the latter in the presence of a palladium dichloride catalyst furnished vinylstannane 98.

With reference to Scheme 6, compound 100, which was protected as TES ether 102 with triethylsilyl triflate. The latter was advanced to alcohol 104 by a four-step sequence analogous to that used for the conversion of 48 to 56 (see Scheme 1) and including a final step of removing the tetrahydropyranyl ether protecting group with magnesium bromide. For Stille coupling purposes, the allylic chloride 106 derived from 104 was found to be more effective than the corresponding bromide (Scheme 1).

Coupling of 98 with 106 (Scheme 7) in the presence of catalytic dipalladium tris(dibenzylideneacetone)chloroform complex and triphenylarsine (Farina. and Krishnan, *J. Am. Chem. Soc.*, 113: 9585, 1991) proceeds in high yield and gives the 9E,12Z,16E-heptadecanoate 108. Exposure of 108 to tetra-n-butylammonium fluoride cleaves both the (trimethylsilyl)ethyl ester and the triethylsilyl ether but leaves tert-butyldimethylsilyl ethers at C3 and C7 intact. The resulting seco acid 110 undergoes facile macrolactonization to 112, and subsequent removal of the remaining pair of TBS ethers with trifluoroacetic acid furnishes trans 9,10 dehydroepothilone D (114).

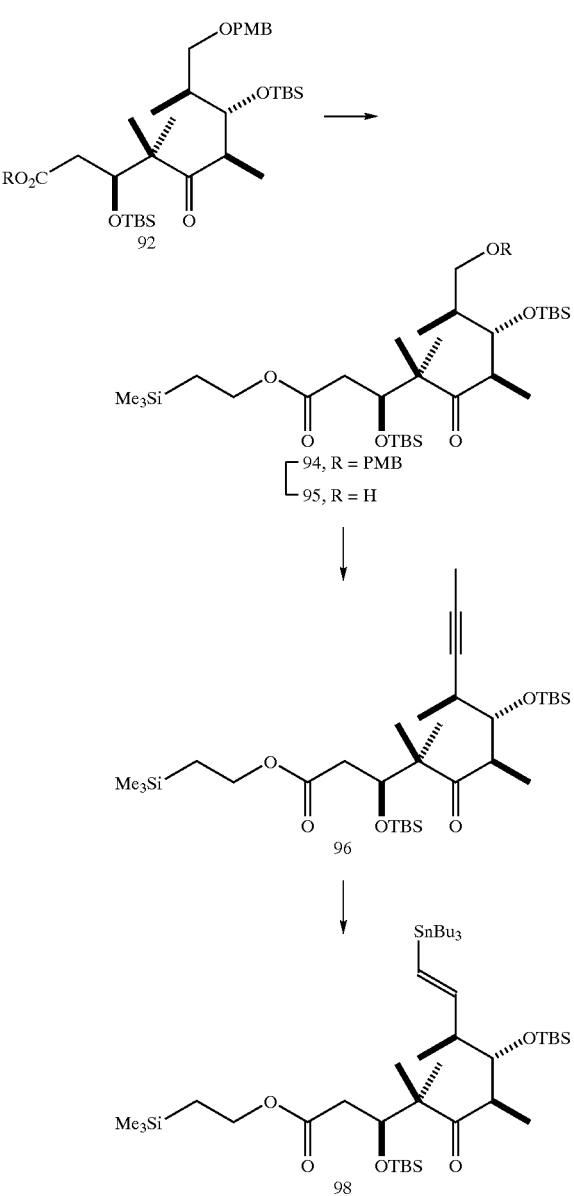

SCHEME 5

SCHEME 6
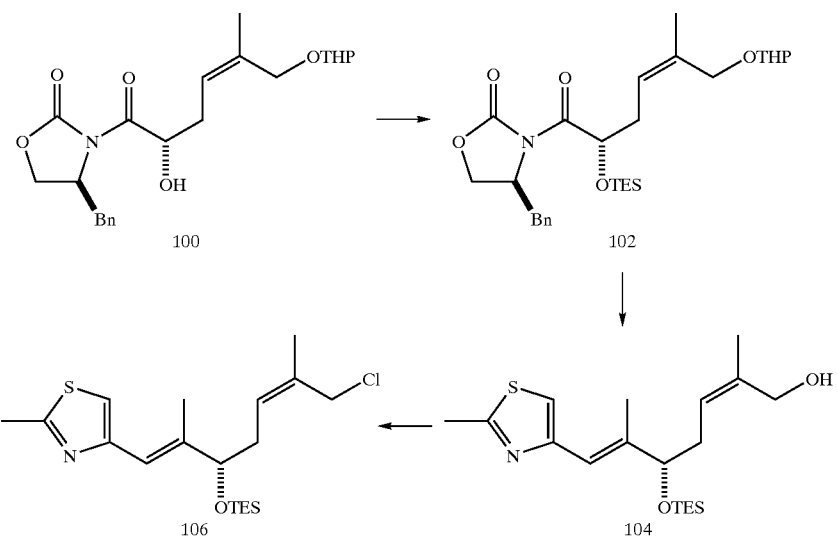
SCHEME 7
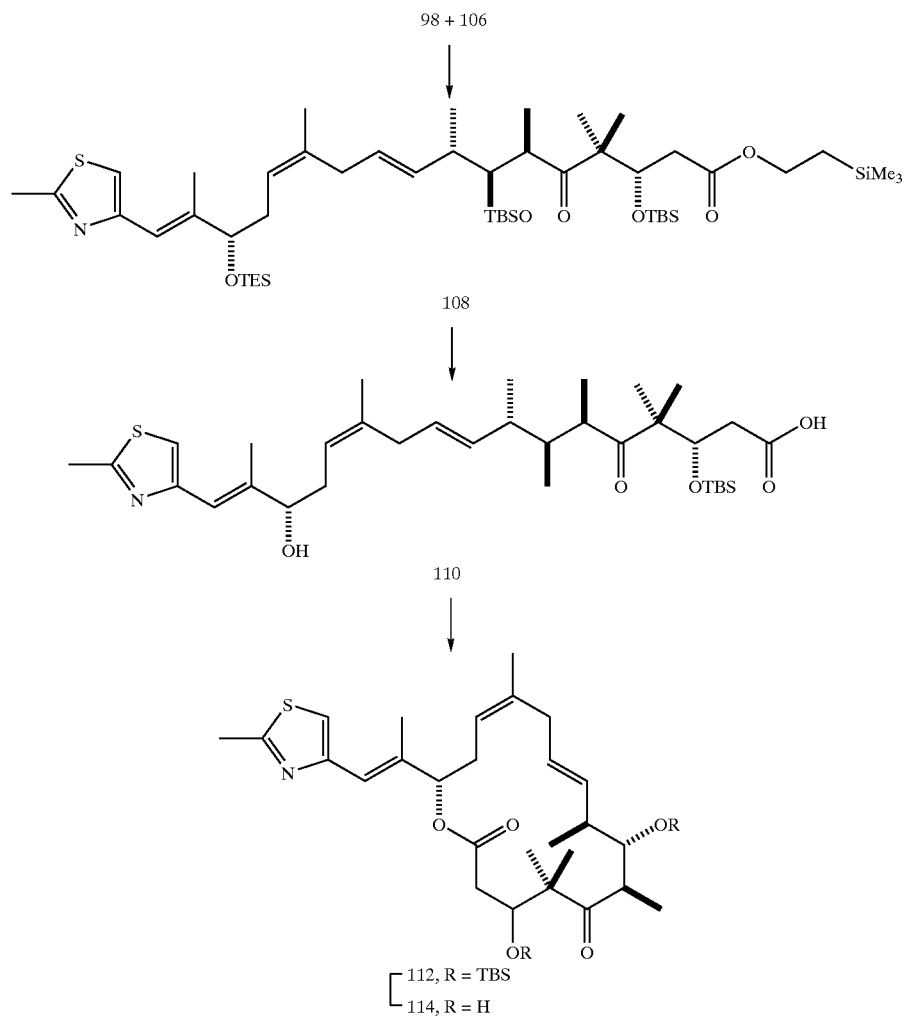

IV. EXAMPLES

The following examples are provided to illustrate certain particular features of working embodiments of the present invention. The scope of the present invention should not be limited to those features described.

Example 1

This example describes the synthesis of compound 44 of Scheme 1. To a stirred solution of the alcohol precursor to 44 (1.03 g, 5.20 mmol) in $CH_2Cl_2$ (20 mL) was sequentially added DHP (580 mg, 630 μL, 6.91 mmol), followed by PPTS (110 mg, 0.438 mmol). After 1.5 hours, the reaction was quenched with solid $NaHCO_3$ (5 g), filtered, concentrated in vacuo and purified by chromatography over silica gel, eluting with 30% $Et_2O$/petroleum ether, to give 44 (1.42 g, 5.00 mmol, 96%) as a colorless oil: IR (neat) 2940, 1445 $cm^{-1}$; $^1H$ NMR (300 MHz, $CDCl_3$) δ 6.04 (s, 1H), 4.62 (t, J=3.0 Hz, 1H), 4.26 (d, J=12.1 Hz, 1H), 4.16 (d, J=12.1 Hz, 1H), 3.85–3.95 (m, 1H), 3.5–3.6 (m, 1H), 1.95 (d, J=1.5 Hz, 3H), 1.5–1.9 (m, 6H); $^{13}C$ NMR (75 MHz, $CDCl_3$) δ 144.6, 98.4, 75.8, 72.1, 62.5, 30.7, 25.6, 22.2, 19.6; HRMS (CI) calculated for $C_9H_{16}O_2$ ($M^+H^+$) 283.0195, found 283.0198.

Example 2

This example describes the synthesis of compound 46. To a stirred solution of t-BuLi (48 mL, 62.4 mmol, 1.3 M in pentane) in $Et_2O$ (63 mL) at −78° C. was added a solution of 44 (10.27 g, 36.4 mmol) in $Et_2O$ (75 mL) via syringe pump over 20 minutes. After 20 minutes, the slurry was rapidly transferred to a precooled solution of CuCN (1.58 mg, 17.7 mmol) in THF (122 mL) at −78° C. After 1 hour at −78° C. and 5 minutes at −40° C., the solution was recooled to −78° C., and a precooled solution of 42 (3.40 g, 14.7 mmol) in THF (86 mL) was added via cannula. An additional amount of THF (25 mL) was added to rinse the flask. After 30 minutes, the solution was warmed to 0° C., and after a further 10 minutes the reaction was quenched with saturated aqueous $NH_4Cl$ (300 mL) and extracted with $Et_2O$ (3×150 mL). The dried ($Mg_2SO_4$) extract was concentrated in vacuo and purified by chromatography over silica gel, eluting with 15–50% $Et_2O$/petroleum ether, to give 46 (5.05 mg, 13.1 mmol, 89%) as a colorless oil: $[α]D^{23}$+46.1 (c 2.58, $CHCl_3$); IR (neat) 1782, 1699 $cm^{-1}$; $^1H$ NMR (300 MHz, $CDCl_3$) δ 7.1–7.4 (m, 5H), 5.40 (t, J=7.1 Hz, 1H), 4.6–4.7 (m, 2H), 4.05–4.2 (m, 4H), 3.8–3.95 (m, 1H), 3.45–3.6 (m, 1H), 3.28 (dd, J=3.2, 13.3 Hz, 1H), 2.9–3.05 (m, 2H), 2.76 (dd, J=9.6, 13.3 Hz, 1H), 2.46 (q, J=7.3 Hz, 2H), 1.5–1.9 (m, 6H), 1.78 (s, 3H); $^{13}C$ NMR (75 MHz, $CDCl_3$) $δ_{172.8}$, 153.6, 135.5, 133.8, 129.6, 129.1, 127.5, 127.4, 97.8, 97.7, 66.4, 65.5, 65.4, 62.3, 55.3, 38.1, 36.0, 30.8, 25.7, 22.7, 21.9, 19.7; HRMS (FAB) calculated for $C_{22}H_{28}NO_5$ ($M^+H^+$) 386.1968, found 386.1965.

Example 3

This example describes the synthesis of compound 48. To a stirred solution of NaHMDS (7.6 mL, 7.6 mmol, 1 M in THF) in THF (35 mL) at −78° C. was added a solution of the alcohol precursor to 46 (2.482 g, 6.41 mmol) in THF (50 mL) via syringe pump over 30 minutes. An additional amount of THF (5 mL) was added to rinse the syringe. After 20 minutes, a precooled solution of oxaziridine (2.55 g, 9.77 mmol) in THF (8 mL) was quickly added via cannula. After 6 minutes, the reaction was quenched with a solution of CSA (3.54 g, 15.2 mmol) in THF (10 mL). After 2 minutes, saturated aqueous $NH_4Cl$ (75 mL) was added. The mixture was allowed to warm to room temperature and was concentrated in vacuo to remove THF. The aqueous layer was extracted with $Et_2O$ (4×100 mL). The dried ($Mg_2SO_4$) extract was concentrated in vacuo and purified by chromatography over silica gel, eluting with 50–70% $Et_2O$/petroleum ether, followed by chromatography over silica gel, eluting with 2–4% acetone/$CH_2Cl_2$, followed by tritration in 10% $Et_2O$/petroleum ether to give 48 (1.84 g, 4.5 mmol, 71%) as a white foam contaminated with a small amount of the phenyl sulfonamide: $[α]D^{23}$+37.2 (c 4.00, $CHCl_3$); IR (neat) 3476, 1781, 1699 $cm^{-1}$; $^1H$ NMR (300 MHz, $CDCl_3$) δ 7.1–7.4 (m, 5H), 5.40 (m, 1H), 5.05–5.15 (m, 1H), 4.55–4.7 (m, 2H), 4.05–4.3 (m, 4H), 4.02 (dd, J=3.7, 11.7 Hz, 1H), 3.8–3.95 (m, 1H), 3.79 (d, J=8.6 Hz, 1H of a diastereomer), 3.66 (d, J=8.6 Hz, 1H of a diastereomer), 3.45–3.6 (m, 1H), 3.31 (dt, J=3.0, 13.5 Hz, 1H), 2.75–2.9 (m, 1H), 2.45–2.6 (m, 2H), 1.5–1.9 (m, 9H); $^{13}C$ NMR (75 MHz, $CDCl_3$) δ 174.6, 174.3, 153.4, 153.3, 136.2, 135.5, 135.11, 135.06, 129.6, 129.2, 127.6, 123.8, 123.1, 98.1, 96.4, 70.5, 70.4, 67.1, 67.0, 65.7, 65.0, 62.4, 61.8, 55.7, 37.7, 32.6, 30.7, 30.5, 25.6, 22.2, 22.1, 19.7, 19.2; HRMS (CI) calculated for $C_{22}H_{28}NO_6$($M^+H^+$) 402.1917, found 402.1919.

Example 4

This example describes the synthesis of compound 50. To a stirred solution of 48 (1.74 g, 4.32 mmol) in $CH_2Cl_2$ (22 mL) at −78° C. was added sequentially 2,6-lutidine (1.06 g, 1.15 mL, 9.87 mmol) followed by TBSOTf (2.07 g, 1.8 mL, 7.83 mmol). After 30 minutes, the reaction was quenched with saturated aqueous $NH_4Cl$ (100 mL) and extracted with $Et_2O$ (4×100 mL). The dried ($Mg_2SO_4$) extract was concentrated in vacuo and purified by chromatography over silica gel, eluting with 30–50% $Et_2O$/petroleum ether, to give 50 (2.06 g, 3.90 mmol, 90%) as a colorless oil: $[α]D^{23}$+32.3 (c 2.96, $CHCl_3$); IR (neat) 1782, 1714 $cm^{-1}$; $^1H$ NMR (300 MHz, $CDCl_3$) δ 7.15–7.4 (m, 5H), 5.35–5.5 (m, 2H), 4.55–4.7 (m, 2H), 4.05–4.2 (m, 2H), 4.0–4.15 (m, 2H), 3.8–3.9 (m, 1H), 3.4–3.5 (m, 1H), 3.36 (d, J=13.1 Hz, 1H), 2.7–2.8 (m, 1H), 2.71 (dt, J=1.6, 10.1 Hz, 1H), 2.45–2.55 (m, 2H), 1.5–1.8 (m, 9H), 0.92 (s, 9H), 0.91 (s, 9H of a diastereomer), 0.11 (s, 3H of a diastereomer), 0.10 (s, 3H of a diastereomer), 0.08 (s, 3H of a diastereomer), 0.07 (s, 3H of a diastereomer); $^{13}C$ NMR (75 MHz, $CDCl_3$) δ 173.9, 173.7, 153.3, 135.5, 134.9, 129.6, 129.1, 127.5, 124.0, 97.6, 96.9, 71.1, 66.7, 65.5, 65.2, 62.3, 61.9, 55.8, 37.9, 34.2, 33.7, 30.8, 30.7, 26.0, 25.7, 22.0, 21.9, 19.7, 19.4, 18.5, −4.6, −4.9; HRMS (CI) calculated for $C_{28}H_{44}NO_6Si$ (M) 518.2938, found 518.2908.

Example 5

This example describes the synthesis of compound 52. To a stirred solution of EtSH (713 mg, 850 FL, 11.5 mmol) in THF (45 mL) was added KH (106 mg, 0.93 mmol, 35% in mineral oil). After 30 minutes, the mixture was cooled to 0° C. and a solution of 50 (2.064 g, 3.99 mmol) in THF (15 mL) was added via cannula over 5 minutes. An additional amount of THF (10 mL) was added to rinse the flask. After 50 minutes at room temperature, the reaction was quenched with saturated aqueous $NH_4Cl$ (50 mL). Air was bubbled through the solution for 2 hours to remove excess ETSH. The solution was extracted with $Et_2O$ (4×100 mL). The dried ($Mg_2SO_4$) extract was concentrated in vacuo and the residue was crystallized by the addition of 10% $Et_2O$/petroleum ether to yield the recovered auxiliary (640 mg, 3.61 mmol, 93%) as a white solid. The decanted solution was purified by chromatography over silica gel, eluting with 10–30% $Et_2O$/ petroleum ether, to give 52 (1.44 g, 3.50 mmol, 90%) as a colorless oil: $[\alpha]D^{23}$ −46.1 (c 3.50, CHCl$_3$); IR (neat) 1684 cm$^{-1}$; $^1$H NMR (300 MHz, CDCl$_3$) 5.35–5.5 (m, 1H), 4.55 (bs, 1H), 3.9–4.2 (m, 3H), 3.8–3.9 (m, 1H), 3.45–3.6 (m, 1H), 2.75–2.9 (m, 2H), 2.4–2.6 (m, 2H), 1.4–1.9 (m, 6H), 1.21 (t, J=7.5 Hz, 3H), 0.93 (s, 9H), 0.09 (s, 3H), 0.06 (s, 3H of a diastereomer), 0.05 (s, 3H of a diastereomer); $^{13}$C NMR (75 MHz, CDCl$_3$) δ 205.1, 205.0, 135.24, 135.16, 97.9, 97.4, 78.6, 65.7, 65.5, 62.3, 62.2, 34.5, 30.8, 25.9, 25.7, 22.6, 22.1, 22.0, 19.7, 19.6, 18.4, 14.8, −4.7, −4.8; HRMS (CI) calculated for C$_{20}$H$_{37}$NO$_4$SSi (M$^+$H$^+$) 401.2182, found 401.2172.

Example 6

This example describes the synthesis of compound 54. To a stirred solution of CuI (4.85 mg, 25.5 mmol) in Et$_2$O (120 mL) at 0° C. was added MeLi (33.1 mL, 23.2 mmol, 1.4 M in Et$_2$O). After 15 minutes, the solution was cooled to −50° C. and a solution of 52 (1.78 g, 4.64 mmol) in Et$_2$O (90 mL) was added via cannula. An additional amount of Et$_2$O (10 mL) was added to rinse the flask. After 30 minutes, the reaction was quenched with saturated aqueous NH$_4$Cl (300 mL) and extracted with Et$_2$O (4×175 mL). The dried (Mg$_2$SO$_4$) extract was concentrated in vacuo and purified by chromatography over silica gel, eluting with 15% Et$_2$O/petroleum ether, to give 54 (1.36 g, 3.81 mmol, 82%) as a colorless oil: $[\alpha]D^{23}$ +14.0 (c 5.00, CHCl$_3$); IR (neat) 1719 cm$^{-1}$; $^1$H NMR (300 MHz, CDCl$_3$) δ 5.35–5.5 (m, 5H), 4.5–4.55 (m, 1H), 3.9–4.1 (m, 3H), 3.75–3.9 (m, 1H), 3.4–3.5 (m, 1H), 2.3–2.5 (m, 2H), 2.10 (s, 3H), 1.74 (s, 3H), 1.4–1.9 (m, 6H), 0.87 (s, 9H), 0.00 (s, 6H); $^{13}$C NMR (75 MHz, CDCl$_3$) δ 135.2, 135.1, 123.8, 123.5, 97.7, 97.3, 79.0, 65.5, 65.2, 62.2, 62.1, 33.2, 30.7, 25.8, 25.6, 25.5, 22.0, 19.6, 19.5, 18.2, −4.8, −4.9; HRMS (CI) calculated for C$_{19}$H$_{37}$O$_4$Si (M$^+$H$^+$) 357.2461, found 357.2455.

Example 7

This example describes the synthesis of compound 56. To a stirred solution of the phosphonate (1.45 g, 5.82 mmol) in THF (10 mL) at −78° C. was added n-BuLi (3.6 mL, 5.76 mmol, 1.6 M in hexanes). After 15 minutes, a solution of 54 (590 mg, 1.66 mmol) in THF (7 mL) was added via cannula. An additional amount of THF (3 mL) was added to rinse the ketone flask. After 30 minutes, the mixture was allowed to warm to room temperature over 1 hour. After an additional 30 minutes, the reaction was quenched with saturated aqueous NH$_4$Cl (50 mL) and extracted with Et$_2$O (4×75 mL). The dried (Mg$_2$SO$_4$) extract was concentrated in vacuo and purified by chromatography over silica gel, eluting with 10–20% Et$_2$O/petroleum ether, to give sequentially the undesired olefin isomer (40 mg, 0.089 mmol, 5%) as a colorless oil followed by the desired product 54 (690 mg, 1.52 mmol, 92%) as a colorless oil: Minor diastereomer: $[\alpha]D^{23}$ −59.2 (c 1.26, CHCl$_3$); IR (neat) 2959, 2852, 1022 cm$^{-1}$; $^1$H NMR (300 MHz, CDCl$_3$) δ 6.79 (s, 1H), 6.18, (s, 1H), 5.35–5.5 (m, 2H), 4.55–4.65 (m, 1H), 4.05–4.15 (m, 2H), 3.8–3.9 (m, 1H), 3.45–3.6 (m, 1H), 2.68 (s, 3H), 2.4–2.5 (m, 1H), 2.2–2.35 (m, 1H), 1.87 (d, J=0.9 Hz, 3H), 1.76 (s, 3H), 1.4–1.9 (m, 6H), 0.84 (s, 9H), 0.07 (s, 3H), −0.10 (s, 3H); $^{13}$C NMR (75 MHz, CDCl3) δ 164.4, 152.9, 143.5, 133.4, 126.7, 126.5, 118.8, 115.2, 97.9, 97.6, 70.8, 70.5, 65.9, 62.4, 62.2, 34.5 ,30.9, 26.0, 25.7, 22.1, 19.8, 19.7, 19.4, 18.5, 18.4, −4.7, −4.9. Major diastereomer: $[\alpha]D^{23}$+ 19.2 (c 3.45, CHCl$_3$); IR (neat) 2959, 1531, 1474 cm$^{-1}$; $^1$H NMR (300 MHz, CDCl$_3$) δ 6.91 (s, 1H), 6.45, (s, 1H), 5.35–5.5 (m, 1H), 4.5–4.6 (m, 1H), 3.9–4.2 (m, 3H), 3.8–3.9 (m, 1H), 3.45–3.6 (m, 1H), 2.70 (s, 3H), 2.2–2.4 (m, 2H), 1.99 (d, J=1.0 Hz, 3H), 1.76 (s, 3H) 1.4–1.9 (m, 6H), 0.88 (s, 9H), 0.04 (s, 3H), −0.01 (s, 3H); $^{13}$C NMR (75 MHz, CDCl3) δ 164.5, 153.4, 142.5, 142.4, 133.6, 126.2, 126.1, 119.2, 118.9, 115.3, 97.8, 97.5, 79.0, 78.9, 65.8,;65.6, 62.3, 62.2, 35.4, 35.3, 30.1, 26.9, 26.0, 25.7, 22.0, 19.7, 19.4, 18.4, 14.1, −4.5, −4.8; HRMS (CI) calculated for C$_{24}$H$_{42}$NO$_3$SSi (M$^+$H$^+$) 452.2655, found 452.2645.

Example 8

This example describes the synthesis of the alcohol precursor to compound 58. To a stirred solution of freshly prepared MgBr$_2$ (27.6 mmol of Mg, 23.8 mmol of BrCH$_2$CH$_2$Br, 50 mL of Et2O) was added 56 (663 mg, 1.26 mmol) in Et$_2$O(5 mL) at room temperature followed by saturated aqueous NH$_4$Cl (approximately 50 μL). After 3.5 hours, the solution was cooled to 0° C. and carefully quenched with saturated aqueous NH$_4$Cl (50 mL). The solution was extracted with Et$_2$O (4×70 mL), and the dried (Mg$_2$SO$_4$) extract was concentrated in vacuo and purified by chromatography over silica gel, eluting with 30–50% Et$_2$O/petroleum ether, to give the desired alcohol (459 mg, 1.26 μmol, 99%) as a colorless oil: $[\alpha]D^{23}$ −16.8 (c 3.40, CHCl$_3$); IR (neat) 3374 cm$^{-1}$; $^1$H NMR (300 MHz, CDCl3) δ 6.92 (s, 1H), 6.44, (s, 1H), 5.31 (t, J=7.7 Hz, 1H), 4.14 (d, J=12.2 Hz, 1H), 4.1–4.2 (m, 1H), 4.00 (d, J=12.2 Hz, 1H), 2.71 (s, 3H), 2.4–2.5 (m, 1H), 2.2–2.3 (m, 2H), 2.00 (s, 3H), 1.80 (s, 3H), 0.89 (s, 9H), 0.06 (s, 3H), 0.04 (s, 3H); $^{13}$C NMR (75 MHz, CDCl3) δ 164.8, 153.0, 142.4, 137.7, 124.4, 119.0, 115.4, 78.4, 62.0, 35.5, 26.0, 22.2, 19.3, 18.5, 14.3, −4.5, −4.7; HRMS (CI) calculated for C$_{19}$H$_{34}$NO$_2$Ssi 368.2080. Found 368.2061.

Example 9

This example describes the synthesis of compound 58. To a stirred solution of the alcohol precursor (620 mg, 1.69 mmol) in CH$_2$Cl$_2$ (5.5 mL) at 0° C. was added Et$_3$N (360 FL, 2.58 mmol) followed by Ms$_2$O (390 μL, 2.24 mmol). After 10 minutes, Me$_2$CO (5.5 mL) was added followed by LiBr (890 mg, 10.3 mmol). After 1.8 hours at room temperature, the mixture was concentrated in vacuo to remove the acetone, diluted with saturated aqueous NH$_4$Cl (100 mL), and extracted with Et$_2$O (4×200 mL). The dried (Mg$_2$SO$_4$) extract was concentrated in vacuo and purified by chromatography over silica gel, eluting with 10–20% Et$_2$O/petroleum ether, to give 58 (607 mg, 1.44 μmol, 84%) as a colorless oil: $[\alpha]D^{23}$+65.1 (c 2.95, CHCl$_3$); IR (neat) 2949, 2930, 2852, 1479, 844 cm$^{-1}$; $^1$H NMR (300 MHz, CDCl3) δ 6.93 (s, 1H), 6.48, (s, 1H), 5.42 (1 dt, J=1.3, 7.6 Hz, H), 4.16 (dd, J=5.4, 7.3 Hz, 1H), 4.06 (d, J=9.5 Hz, 1H), 3.90 (d, J=9.5 Hz, 1H), 2.71 (s, 3H), 2.3–2.5 (m, 2H), 2.01 (d, J=1.1 Hz, 3H), 1.83 (d, J=1.0 Hz, 3H), 0.88 (s, 9H), 0.04 (s, 3H), 0.01 (s, 3H); $^{13}$C NMR (75 MHz, CDCl3) δ 164.6, 153.2, 142.1, 133.3, 128.2, 119.2, 115.4, 78.1, 35.7, 32.6, 26.0, 22.2, 19.4, 18.4, 13.1, −4.5, −4.8; HRMS (CI) calculated for C$_{l9}$H$_{33}$NO$_2$SSi$_{81}$Br (M$^+$H$^+$) 430.1235, found 430.1244.

Example 10

This example describes the synthesis of compound 60. To a stirred solution of Ph$_3$PMeBr (1.53 g, 4.28 mmol) in THF (16.2 mL) at −78° C. was added n-BuLi (2.7 mL, 4.32 mmol, 1.6 M in hexanes) over a period of 3 minutes. After 35 minutes, a precooled solution of 58 (607 mg, 1.41 mmol) in THF (7 mL) was added dropwise to the ylide over a period of 5 minutes. An additional portion of THF (6 mL) was added to rinse the flask. After 15 minutes, the mixture was allowed to warm to −20° C. After an additional 20 minutes, the reaction was quenched with MeOH, and was concentrated in vacuo. The residue was purified by chromatography over silica gel, eluting with 0–6% MeOH/CH$_2$Cl$_2$, followed by dilution with CH$_2$Cl$_2$ and an H$_2$O wash to remove excess Ph$_3$MeBr, to give 60 (890 mg, 1.26 mmol, 89%) as an off-white foam: [α]$_D^{23}$+6.4 (c 1.06, CHCl3); IR (neat) 2959, 2930, 2853, 1440; $^1$H NMR (300 MHz, CDCl$_3$) δ 7.6–7.9 (1 m, 5H), 6.89 (s, 1H), 6.33, (s, 1H), 5.20 (m, 1H), 3.95 (m, 1H), 3.5–3.8 (m, 2H), 2.65 (s, 3H), 2.1–2.3 (m, 2H), 1.88 (s, 3H), 1.83 (s, 3H), 0.78 (s, 9H), −0.07 (s, 3H), −0.09 (s, 3H); $^{13}$C NMR (75 MHz, CDCl$_3$) δ 164.7, 153.0, 142.1, 135.6, 133.9, 130.9, 130.7, 124.7, 118.8, 117.5, 115.6, 78.2, 35.9, 26.0, 24.7, 23.7, 22.6, 21.9, 19.4, 18.3, 14.4, −4.6, −4.8; HRMS (CI) calculated for C$_{38}$H$_{49}$NOPSSi (M$^+$H$^+$) 626.3042, found 626.3028.

Example 11

This example describes the synthesis of compound 66. To a stirred solution of i-Pr$_2$NH (390 μL, 2.78 mmol) in THF (0.7 mL) was added n-BuLi (1.73 mL, 2.77 mmol, 1.6 M in hexanes) dropwise at −78° C. After 5 minutes, the solution was warmed to 0° C. for 45 minutes and recooled to −78° C. To the stirring solution of LDA was added a precooled solution of 62 (718 mg, 2.53 mmol) in THF (0.6 mL) dropwise via cannula over 5 minutes. An additional amount of THF (0.4 mL) was used to rinse the flask. After an additional 50 minutes at −78° C., a precooled solution of 64 (484 mg, 2.33 mmol) in THF (0.6 mL) was added dropwise via cannula. An additional amount of THF (0.4 mL) was used to rinse the flask. After 30 minutes, the reaction was quenched with saturated aqueous NH$_4$Cl (20 mL) and extracted with Et$_2$O (4×25 mL). The dried (Mg$_2$SO$_4$) extract was concentrated in vacuo and purified by chromatography over silica gel, eluting with 6–10% Et$_2$O/petroleum ether, to give 66 (694 mg, 1.41 mmol, 61%) as a colorless oil: [α]$_D^{23}$−25.1 (c 3.05, CHCl3); IR (neat) 3483, 1695 cm$^{-1}$; $^1$H NMR (300 MHz, CDCl$_3$) δ 7.25 (d, J=8.7 Hz, 2H), 6.86 (d, J=8.7 Hz, 2H), 5.65–5.85 (m, 1H), 4.9–5.1 (m, 2H),:4.44 (s, 2H), 3.93 (dd, J=4.5, 6.4 Hz, 1H), 3.80 (s, 3H), 3.55–3.65 (m, 3H), 3.46 (dd, J=6.1, 8.9 Hz, 1H), 3.15–3.25 (m, 1H), 2.05–2.2 (m, 2H), 1.8–1.9 (m, 1H), 1.18 (s, 3H), 1.11 (s, 3H), 1.05 (d, J=6.8 Hz, 3H), 0.94 (d, J=7.9 Hz, 3H), 0.89 (s, 9H), 0.07 (s, 3H), 0.06 (s, 3H); $^{13}$C NMR (75 MHz, CDCl$_3$) δ 221.7, 159.3, 136.5, 130.9, 129.4, 116.9, 113.9, 73.2, 73.1, 72.9, 55.4, 54.4, 41.9, 39.8, 36.4, 29.9, 26.3, 23.9, 19.3, 18.4, 14.3, 10.2, −3.3, −3.8; HRMS (CI) calculated for C$_{28}$H$_{49}$O$_5$Si (M$^+$H$^+$) 493.3349, found 493.3350.

Example 12

This example describes the synthesis of compound 68. To a stirred solution of 66 (61 mg, 0.124 mmol) in CH$_2$Cl$_2$ (0.7 mL) at 0° C. was sequentially added Et$_3$N (29 mg, 40 μL, 0.287 mmol) followed by TBSOTf (43.7 mg, 38 μL, 0.165 mmol) at 0° C. After 45 minutes, the reaction was quenched with saturated aqueous NH$_4$Cl (20 mL) and extracted with Et$_2$0 (4×25 mL). The dried (Mg$_2$SO$_4$) extract was concentrated in vacuo and purified by chromatography over silica gel, eluting with 3–10% Et$_2$0/petroleum ether, to give 68(66.5 mg, 0.111 mmol, 89%) as a colorless oil: [α]$_D^{23}$−16.0 (c 2.92, CHCl$_3$); IR (neat) 1695 cm$^{-1}$; $^1$H NMR (300 MHz, CDCl$_3$) δ 7.23 (d, J=8.6 Hz, 2 h), 6.86 (d, J=8.6 Hz, 2 h), 5.7–5.9 (m, 1H), 4.99 (d, J=6.4 Hz, 1H), 4.95 (s, 1H), 4.40 (s, 2H), 3.9–4.0 (m, 1H), 3.85 (d, J=7.3 Hz, 1H), 3.80 (s, 3), 3.58 (dd, J=5.7, 9.2 Hz, 1H), 3.27 (qn, J=7.4 Hz, 1H), 3.19 (t, J=7.4 Hz, 1H) 2.0–2.2 (m, 2H), 1.8–1.9 (m, 1H), 1.13 (s, 3H), 1.04 (s, 3H), 1.02 (3H, d, J=7.0 Hz) 0.96 (3H, d, J=6.9 Hz), 0.891 (s, 9H), 0.887 (s, 9H), 0.06 (s, 6H), 0.05 (s, 3H), 0.03 (s, 3H); $^{13}$C NMR (75 MHz, CDCl$_3$) δ 219.2, 159.3, 137.1, 131.0, 129.5, 116.5, 113.9, 76.5, 73.1, 71.8, 55.5, 54.2, 46.2, 39.8, 38.9, 26.5, 26.3, 25.3, 18.7, 18.4, 18.0, 17.0, 16.6, −3.0, −3.3, −3.5, −3.8; HRMS (CI) calculated for C$_{34}$H$_{63}$O$_5$Si$_2$ (M$^+$H$^+$) 607.4214, found 607.4212.

Example 13

This example describes the synthesis of compound 70. To a stirred solution of 68(722 mg, 1.19 mmol) in THF (9 mL) and H$_2$0 (8.5 mL) was sequentially added OSO$_4$ (400 μL, 4% in H$_2$0) followed by NaIO$_4$ (1.065 g, 4.98 mmol). After 18 hours, the reaction was quenched with saturated aqueous Na$_2$S$_2$O$_3$ (50 mL). After 30 minutes, saturated aqueous NaCl (100 mL) was added and the mixture was extracted with Et$_2$O (4×100 mL). The dried (Mg$_2$SO$_4$) extract was concentrated in vacuo to give the aldehyde as a colorless oil: [α]$_D^{23}$−13.0 (c 4.20, CHCl$_3$); IR (neat) 1725, 1689 cm$^{-1}$; $^1$H NMR (300 MHz, CDCl$_3$) δ 9.74 (1 t, J=1.2 Hz, 1H), 7.22 (d, J=8.5 Hz, 2 h), 6.85 (d, J=8.5 Hz, 2H), 4.46 (t, J=5.3 Hz, 1H), 4.39 (s, 2H), 3.82 (d, J=7.9 Hz, 1H), 3.80 (s, 3H), 3.58 (dd, J=6.0, 9.1 Hz, 1H), 3.27 (qn, J=7.4 Hz, 1H), 3.19 (dd, J=6.9, 8.9 Hz, 1H) 2.3–2.5 (m, 2H), 1.6–1.8 (m, 1H), 1.14 (s, 3H), 1.06 (s, 3H), 1.00 (d, J=7.0 Hz, 3H), 0.94 (d, J=7.0 Hz, 3H), 0.88 (s, 9H), 0.87 (s, 9H), 0.08 (s, 3H), 0.05 (s, 6H), 0.03 (s, 3H); $^{13}$C NMR (75 MHz, CDCl$_3$) δ 219.0, 201.5 159.3, 130.9, 129.5, 113.9, 76.8, 73.1, 71.7, 71.6, 55.4, 53.7, 49.7, 46.2, 38.8, 26.4, 26.1, 24.4, 18.7, 18.3, 17.0, 15.7, −3.4, −3.5, −3.9, −4.3; HRMS (CI) calculated for C$_{33}$H$_{61}$O$_6$Si$_2$ (M$^+$H$^+$) 609.4007, found 607.4005.

To a stirred solution of the crude aldehyde (1. 19 mmol) prepared above in t-BuOH (16 mL) and H$_2$O (15 mL) was sequentially added 2-methyl-2-butene (3 mL) followed by NaH$_2$PO$_4$ (1.06 g, 11.6 mmol) and NaClO$_2$ (490 mg, 5.4 mmol). After 1 hour, the reaction was quenched with saturated aqueous NaCl (75 mL) and extracted with Et2O (4×100 mL). The dried (Mg$_2$SO$_4$) extract was concentrated in vacuo to give crude 70 as a colorless oil: [α]$_D^{23}$−26.8 (c 4.20, CHCl$_3$); IR (neat) 2400–3400, 1722 cm$^{-1}$; $^1$H NMR (300 MHz, CDCl$_3$) δ 7.23 (d, J=8.6 Hz, 2H), 6.85 (d, J=8.6 Hz, 2H), 4.40 (s, 2H), 4.3–4.4 (m, 1H), 3.82 (d, J=7.9 Hz, 1H), 3.80 (s, 3H), 3.58 (dd, J=5.8, 9.1 Hz, 1H), 3.32 (qn, J=7.2 Hz, 1H), 3.18 (dd, J=7.2, 8.9 Hz, 1H) 2.46 (dd, J=2.9, 16.4 Hz, 1H), 2.28 (dd, J=6.8, 16.4 Hz, 1H), 1.7–1.85 (m, 1H), 1.15 (s, 3H), 1.07 (s, 3H), 1.02 (d, J=6.9 Hz, 3H), 0.95 (d, J=7.0 Hz, 3H), 0.88 (s, 9H), 0.87 (s, 9H), 0.08 (s, 3H), 0.05 (s, 6H), 0.04 (s, 3H); $^{13}$C NMR (75 MHz, CDCl$_3$) δ 218.7, 178.0, 159.3, 129.5, 113.9, 73.8, 73.1, 71.7, 55.5, 53.7, 46.3, 40.4, 38.9, 26.4, 26.4, 26.2, 24.0, 18.7, 18.4, 17.0, 15.8, −3.3, −3.5, −4.1, −4.4; HRMS (CI) calculated for C$_{33}$H$_{61}$O$_7$Si$_2$ 625.3966. Found 625.3957.

Example 14

This example describes the synthesis of compound 72. To a stirred solution of crude 70 (1.19 mmol) in PhH (20 mL) and MeOH (2.5 mL) was added TMSCHN$_2$ (700 μL, 1.4 mmol, 2 M in hexanes). After 45 minutes, the mixture was concentrated in vacuo and purified by chromatography over silica gel, eluting with 5–10% Et$_2$O/petroleum ether, to give 72 (502 mg, 0.797 mmol, 66% over three steps) as a colorless oil: [α]$_D^{23}$−27.1 (c 1.03, CHCl$_3$); IR (neat) 1741, 1690 cm$^{-1}$; $^1$H NMR (300 MHz, CDCl$_3$) δ 7.23 (d, J=8.5 Hz, 2H), 6.86 (d, J =8.5 Hz, 2H), 4.39 (s, 2H), 4.3–4.4 (m, 1H), 3.83 (d, J=7.8 Hz, 1H), 3.80 (s, 3H), 3.66 (s, 3H), 3.58 (dd, J=5.7, 9.1 Hz, 1H), 3.31 (qn, J=7.2 Hz, 1H), 3.18 (dd, J=7.3, 9.1 Hz, 1H), 2.46 (dd, J=3.1, 16.1 Hz, 1H), 2.26 (dd, J=7.0, 16.1 Hz, 1H), 1.7–1.85 (m, 1H), 1.14 (s, 3H), 106 (s, 3H), 1.01 (d, J=6.9 Hz, 3H), 0.95 (d, J=6.9 Hz, 3H), 0.88 (s, 9H), 0.87 (s, 9H), 0.08 (s, 3H), 0.05 (s, 6H), 0.02 (s, 3H); $^{13}$C NMR (75 MHz, CDCl$_3$) δ 218.5, 172.7, 159.3, 131.0, 129.5, 113.9, 74.1, 73.1, 71.8, 55.5, 53.6, 51.8, 46.3, 40.4, 38.9, 26.5, 26.2, 24.0, 18.8, 18.7, 18.4, 17.0, 15.7, −3.3, −3.5, −4.3, −4.4; HRMS (CI) calculated for C$_{33}$H$_{63}$O$_7$Si$_2$ (M$^+$H$^+$) 639.4112, found 639.4112.

Example 15

This example describes the synthesis of compound 74. To a stirred solution of 72 (290 mg, 0.455 mmol) in EtOH (7 mL) was added palladium on carbon (101 mg, 10% Pd) and the mixture was placed under an atmosphere of H$_2$. After 0.75 hour, the H$_2$ atmosphere was replaced by Ar and the reaction was filtered through Celite (EtOH rinse). The liquid was concentrated in vacuo and the residue was purified by chromatography over silica gel, eluting with 10–30% Et$_2$O/petroleum ether, to give 74 (216 mg, 0.418 mmol, 92%) as a colorless oil: [α]D$^{23}$−13.2 (c 1.07, CHCl$_3$); IR (neat) 3538, 1743, 1694 cm$^{−1}$; $^1$H NMR (300 MHz, CDCl$_3$) δ4.40 (dd, J=2.9, 6.9 Hz, 1H), 3.93 (dd, J=2.0, 7.8 Hz, 1H), 3.67 (s, 3H), 3.6–3.7 (m, 1H), 3.5–3.6 (m, 1H), 3.31 (qn, J=7.5 Hz, 1H), 2.43 (dd, J=2.7, 16.3 Hz, 1H), 2.26 (dd, J=6.9, 16.3 Hz, 1H), 1.55–1.65 (m, 1H), 1.22 (s, 3H), 1.13 (s, 3H), 1.09 (d, J=7.0 Hz, 3H), 0.95 (d, J=7.1 Hz, 3H), 0.92 (s, 9H), 0.87 (s, 9H), 0.12 (s, 3H), 0.10 (s, 3H), 0.09 (s, 3H), 0.01 (s, 3H); $^{13}$C NMR (75 MHz, CDCl$_3$) δ 218.4, 172.8, 78.2, 73.6, 64.9, 53.9, 51.9, 47.0, 40.3, 39.8, 29.9, 26.4, 26.2, 24.1, 19.1, 18.6, 18.4, 16.1, −3.4, −3.6, −4.3, −4.4; HRMS (CI) calculated for C$_{26}$H$_{53}$Si$_2$O$_6$ (M$^+$H$^+$) 517.3381, found 517.3361.

Example 16

This example describes the synthesis of compound 76. To a stirred solution of 74(700 mg, 1.36 mmol) and powdered molecular sieves (1.5 g) in CH$_2$Cl$_2$ (35 mL) was sequentially added NMO (420 mg, 3.56 mmol) followed by TPAP (137.5 mg, 106 mmol). After 1 hour, the mixture was diluted with 30% Et$_2$O/petroleum ether (100 mL) and filtered through silica gel (30% Et$_2$O/petroleum ether rinse). The filtrate was concentrated in vacuo to give 76 (698 mg, 1.36 mmol, 99%) as a colorless oil: [α]D$^{23}$−32.1 (c 1.76, CHCl$_3$); IR (neat) 1746, 1690 cm$^{−1}$; $^1$H NMR (300 MHz, CDCl$_3$) δ 9.73 (d, J=2.1 Hz, 1H), 4.41 (dd, J=3.2, 6.9 Hz, 1H), 4.08 (dd, J=2.1, 8.3 Hz, 1H), 3.67 (s, 3H), 3.25 (qn, J=7.0 Hz, 1H), 2.41 (1Hdd, J=3.3, 16.1 Hz, 1H), 2.2–2.35 (m, 2H), 1.24 (s, 3H), 1.12 (d, J=7.1 Hz, 3H), 1.10 (d, J=6.9 Hz, 3H), 1.09 (s, 3H), 0.89 (s, 9H), 0.87 (s, 9H), 0.11 (s, 3H), 0.090 (s, 3H), 0.085 (s, 3H), 0.01 (s, 3H); $^{13}$C NMR (75 MHz, CDCl$_3$) δ 218.0, 204.4, 172.6, 76.5, 73.9, 53.8, 51.9, 51.0, 46.8, 40.4, 29.9, 26.4, 24.0, 19.2, 18.6, 18.4, 15.9, 12.7, −3.4, −3.6, −4.3, −4.4; HRMS (CI) calculated for C$_{26}$H$_{51}$Si$_2$O$_6$ (M$^+$H$^+$) 515.3225, found 515.3218.

Example 17

This example describes the synthesis of compound 78. To LHMDS [HMDS (280 μL, 1.31 mmol) in THF (650 μL) at −78° C. was added n-BuLi (820 μL, 1.31 mmol, 1.6 M in hexanes). After 5 minutes, the solution was warmed to 0° C. and added dropwise to a stirred solution of the salt 58 (930 mg, 1.32 mmol) in THF (17 mL) at −78° C. via cannula. After 15 minutes, the solution was warmed to −30° C. After an additional 15 minutes, the solution was re-cooled to −78° C. and added dropwise to a pre-cooled solution of the 76 (520 mg, 1.03 mmol) in THF (0.6 mL) via cannula. The mixture was then allowed to warm slowly to room temperature over a period of 1 hour. After 10 minutes at room temperature, the reaction was quenched with saturated aqueous NH$_4$Cl (25 mL) and was concentrated in vacuo to remove THF. The solution was extracted with Et$_2$O (4×50 mL), and the dried (Mg$_2$SO$_4$) extract was concentrated in vacuo and purified by chromatography over silica gel, eluting with 2–10% Et$_2$O/petroleum ether, to give 78 (728 mg, 0.84 mmol, 82%) as a colorless oil: [α]D$^{23}$+3.6 (c 1.00, CHCl$_3$); IR (neat) 1743, 1699 cm$^{−1}$; $^1$H NMR (300 MHz, CDCl$_3$) δ 6.91 (s, 1H), 6.45 (s, 1H), 5.58 (t, J=9.2 Hz, 1H), 5.2–5.35 (m, 1H), 5.16 (t, J6.6Hz, 1H), 4.39 (1H, dd, J=3.1, 6.9 Hz), 4.09 (1H, t, J=6.6 Hz), 3.8–3.9 (m, 1H), 3.6–3.7 (m, 1H); 3.66 (s, 3H), 3.03 (qn, J=6.7 Hz, 1H), 2.70 (s, 3H), 2.65–2.75 (m, 2H), 2.3–2.5 (m, 2H), 2.15–2.35 (m, 3H), 1.99 (s, 3H), 1.64 (s, 3H), 1.19 (s, 3H), 1.06 (s, 3H), 1.03 (d, J=7.1 Hz, 3H), 1.00 (d, J=7.0 Hz, 3H), 0.92 (s, 9H), 0.88 (s, 9H), 0.86 (s, 9H), 0.08 (s, 3H), 0.07 (s, 6H), 0.04 (s, 3H), 0.00 (s, 3H), −0.01 (s, 3H); $^{13}$C NMR (75 MHz, CDCl$_3$) δ 218.0, 172.6, 164.5, 153.4, 142.5, 135.5, 131.7, 128.7, 122.2, 119.0, 115.2, 79.1, 76.1, 74.2, 53.5, 51.8, 46.4, 40.4, 37.9, 35.6, 30.9, 26.4, 26.2, 26.0, 24.0, 23.9, 19.4, 19.3, 18.7, 18.4, 14.9, 14.1, −3.3, −3.7, −4.3, −4.4, −4.7; HRMS (CI) calculated for C$_{46}$H$_{86}$O$_6$Si$_3$SN (M$^+$H$^+$) 864.5484, found 864.5510.

Example 18

This example describes the synthesis of compound 80. To a stirred solution of 78(51 mg, 59 μmol) in i-PrOH (1 mL) was added NaOH (11.5 FL, 62 μmol, 5.4 M in H$_2$O), and the mixture was heated at 45° C. in a sealed tube. After 16 hours, the solution was concentrated, diluted with aqueous HCl (20 mL, 0.5 M) and extracted with Et$_2$O (4×50 mL). The dried (Mg$_2$SO$_4$) extract was concentrated in vacuo and purified by chromatography over silica gel, eluting with 5–20% EtOAc/hexanes, to give 80 (33 mg, 34 Fmol, 66%) as a colorless oil: IR (neat) 3500–2500, 1713 cm$^{−1}$; $^1$H NMR (300 MHz, CDCl$_3$) δ 6.93 (s, 1H), 6.67 (s, 1H), 5.52 (t, J=9.6 Hz, 1H), 5.3–5.4 (m, 1H), 5.23 (t, J=7.4 Hz, 1H), 4.41 (dd, J=3.3, 6.6 Hz, 1H), 3.75–3.85 (m, 1H), 2.9–3.1 (m, 2H), 2.71 (s, 3H), 2.5–2.8 (m, 2H), 2.1–2.6 (m, 4H), 1.9–2.1 (m, 1H), 1.93 (s, 3H), 1.71 (s, 3H), 1.16 (s, 3H), 1.13 (s, 3H), 1.04 (d, J=7.0 Hz, 3H), 9.94 (obscured d, 3H), 0.92 (s, 9H), 0.88 (18H, s), 0.12 (s, 6H), 0.09 (s, 3H), 0.06 (s, 3H), 0.03 (s, 3H), −0.01 (s, 3H); HRMS (CI) calculated for C$_{45}$H$_{84}$O$_6$Si$_3$SN (M$^+$H$^+$) 850.5327, found 850.5281.

Example 19

This example describes the synthesis of compound 82. To a stirred solution of 80 (154 mg, 181 μmol) in THF (3.9 mL) at 0° C. was added TBAF (1.1 mL, 1.1 mmol, 1 M in THF). The solution was allowed to warm slowly to room temperature overnight. After 16 hours, the mixture was diluted with EtOAc, washed with saturated aqueous NH$_4$Cl (50 mL), and extracted with EtOAc (4×100 mL). The dried (Mg$_2$SO$_4$) extract was concentrated in vacuo and purified by chromatography over silica gel, eluting with 2–5% MeOH/CH$_2$Cl$_2$, to give 82 (118.5 mg, 160 μmol, 89%) as a white foam: [α]D$^{23}$−2.6 (c 3.50, CHCl$_3$); IR (neat) 3500–2500, 1709 cm$^{−1}$; $^1$H NMR (300 MHz, CDCl$_3$) δ 6.95 (s, 1H), 6.70 (s, 1H), 5.56 (t, J=10.0 Hz, 1H), 5.3–5.45 (m, 1H), 5.24 (t, J=7.3 Hz, 1H), 4.35–4.45 (m, 1H), 4.16 (t, J=6.2 Hz, 1H), 3.75–3.85 (m, 1H), 3.03 (m, 2H), 2.75–2.85 (m, 1H), 2.72 (s, 3H), 2.65–2.75 (m, 1H), 2.2–2.7 (m, 5H), 1.99 (s, 3H), 1.74 (s, 3H), 1.15 (s, 3H), 1.14 (s, 3H), 1.04 (d, J=7.1 Hz, 3H), 0.98 (d, J=6.9 Hz, 3H), 0.92 (s, 9H), 0.87 (s, 9H), 0.12 (s, 3H), 0.10 (s, 3H), 0.07 (s, 3H), 0.06 (s, 3H); $^{13}$C NMR (75 MHz, CDCl$_3$) δ 218.1, 176.0, 165.1, 152.4, 141.9, 137.5, 131.6, 127.8, 120.8, 118.8, 115.1, 77.2, 76.0, 73.5, 53.6, 46.3, 40.1, 38.0, 34.1, 30.8, 26.2, 26.0, 23.7, 23.5, 19.0, 18.9, 18.7, 18.5, 18.1, 15.0, 14.6, −3.6, −4.1, −4.2, −4.6; HRMS (CI) calculated for C$_{39}$H$_{70}$O$_6$Si$_2$SN (M$^+$H$^+$) 736.4462, found 736.4451.

Example 20

This example describes the synthesis of the protected alcohol precursor to compound 84. To a stirred solution of 82 (57.2 mg, 78.0 μmol) in THF (1.3 mL) at 0° C. was added Et₃N (19 FL, 136 μmol) followed by 2,4,6-trichlorobenzoyl chloride (14 μL, 89.5 mmol). After 45 minutes, the mixture was diluted with THF (1 mL) and PhMe (1.7 mL) and was added via syringe pump to a stirring solution of DMAP (16.3 mg, 133 μmol) in PhMe (18 mL) at 75° C. over a period of 3.5 hours. After an additional 1 hour, the solution was cooled, diluted with EtOAc, washed with saturated aqueous NH₄Cl (50 mL), and extracted with EtOAc (4×100 mL). The dried (Mg₂SO₄) extract was concentrated in vacuo and purified by chromatography over silica gel, eluting with 2–10% EtOAc/hexanes, to give the protected alcohol precursor to compound 84 (35.5 mg, 49.5 μmol, 63%) as a colorless oil contaminated with a small amount of an oligomer: IR (neat) 1738, 1709 cm$^{-1}$; $^1$H NMR (300 MHz, CDCl₃) δ 6.95 (s, 1H), 6.50 (s, 1H), 5.65 (t, J=10.0 Hz, 1H), 5.3–5.45 (m, 2H), 5.11 (t, J=6.3 Hz, 1H), 4.45 (dd, J=2.8, 8.0 Hz, 1H), 3.7–3.8 (m, 1H), 3.19 (dd, J=9.5, 15.7 Hz, 1H), 3.0–3.1 (m, 1H), 2.71 (s, 3H), 2.2–2.7 (m, 6H), 2.09 (s, 3H), 1.74 (s, 3H), 1.13 (s, 3H), 1.11 (s, 3H), 1.07 (d, J=7.1 Hz, 3H), 0.99 (d, J=7.0 Hz, 3H), 0.93 (s, 9H), 0.87 (s, 9H), 0.14 (s, 3H), 0.11 (s, 3H), 0.07 (s, 3H), 0.06 (s, 3H); $^{13}$C NMR (75 MHz, CDCl₃) δ 216.0, 169.9, 164.9, 152.9, 137.8, 136.5, 130.8, 126.9, 121.1, 118.9, 116.6, 106.3, 78.1, 76.4, 73.1, 54.0, 47.4, 41.2, 39.0, 31.0, 26.4, 26.3, 26.1, 24.5, 21.3, 20.5, 19.7, 19.5, 18.9, 18.3, 15.2, 14.7, −3.4, −3.5, −4.6; HRMS (CI) calculated for C₃₉H₆₈O₅Si₂SN (M$^+$H$^+$) 718.4357, found 718.4354.

Example 21

This example describes the synthesis of compound 84. To a stirred solution of the protected alcohol precursor to compound 82 (16.5 mg, 23 mmol) in CH₂Cl₂ (110 μL) at 0° C. was added TFA (100 μL). After 4.5 hours, the mixture was concentrated in vacuo and purified by chromatography over silica gel, eluting with 20–50% EtOAc/hexanes, to give 84 (9.3 mg, 19 Fmol, 83%) as a colorless oil: [α]D$^{23}$−133.0 (c 1.30, CHCl₃); IR (neat) 3438, 1738, 1694 cm$^{-1}$; $^1$H NMR (400 MHz, CDCl₃) δ 6.97 (s, 1H), 6.52 (s, 1H), 5.5–5.7 (m, 2H), 5.35–5.45 (m, 1H), 5.15 (t, J=7.1 Hz, 1H), 4.22 (dd, J=2.5, 9.4 Hz, 1H), 3.7–3.8 (m, 1H), 3.1–3.2 (m, 1H), 3.04 (dd, J=7.7, 15.3 Hz, 1H), 2.85–2.95 (m, 1H), 2.70 (s, 3H), 2.4–2.7 (m, 6H), 2.06 (s, 3H), 1.72 (s, 3H), 1.27 (s, 3H), 1.1–1.2 (obscured d, 3H×2), 1.12 (s, 3H); $^{13}$C NMR (100.5 MHz, CDCl₃) δ 220.4, 170.7, 152.2, 138.1, 137.0, 132.3, 128.1, 119.0, 118.9, 115.7, 77.4, 74.1, 73.0, 52.7, 44.2, 39.1, 36.9, 31.4, 30.2, 29.7, 23.9, 21.8, 20.4, 19.0, 17.5, 16.0, 13.3; HRMS (CI) calculated for C₂₇H₄₀O₅SN (M$^+$H$^+$) 490.2627, found 490.2627.

Example 22

This example describes the synthesis of 86. To a stirred solution of 84 (6.6 mg, 13.5 μmol) in CH₂Cl₂ (2 mL) at reflux was added portionwise a large excess of KO₂CN=NCO₂K followed by AcOH (2 equivalents) until the reaction was complete by TLC (25 hours). The KOAc precipitate was periodically removed during the course of the reaction. The solution was filtered through SiO₂ (Et₂O rinse), concentrated in vacuo, and purified by chromatography over silica gel, eluting with EtOAc/hexanes/CH₂Cl₂ (1:4:5–1:1:2), to give 86 (3.4 mg, 6.9 μmol, 52%) as a colorless oil: [α]D$^{23}$−86.7 (c 0.15, CHCl₃); $^1$H NMR (400 MHz, CDCl₃) δ 6.95 (s, 1H), 6.58 (s, 1H), 5.22 (d, J=8.8 Hz, 1H), 5.1–5.2 (m, 1H), 4.30 (d, J=11.2 Hz, 1H,), 3.7–3.8 (m, 1H), 3.4–3.55 (m, 1H), 3.15 (q, J=4.8 Hz, 1H), 3.0–3.1 (m, 1H), 2.69 (s, 3H), 2.5–2.7 (m, 1H), 2.05–2.5 (m, 4H), 2.06 (s, 3H), 1.8–1.9 (m, 1H), 1.7–1.8 (m, 1H), 1.34 (s, 3H), 1.2–1.3 (m, 4H), 1.19 (d, J=7.0 Hz, 3H), 1.07 (s, 3H), 1.01 (d, J=6.9, 3H); $^{13}$C NMR (100.5 MHz, CDCl₃) δ 220.8, 170.6, 165.2, 152.3, 139.4, 138.7, 121.1, 119.5, 115.9, 79.2, 74.4, 72.6, 53.7, 42.0, 39.9, 32.8, 32.0, 31.9, 25.6, 23.1, 19.3, 18.3, 16.1, 16.0, 13.6.

Example 23

This example describes the synthesis of compound 4. To a stirred solution of 86 (1.5 mg, 3.05 mmol) in CH₂Cl₂ (400 mL) at −50° C. was added a solution of dimethyl dioxirane until all of the starting material had been consumed as judged by TLC. The solution was concentrated in vacuo and purified by chromatography over silica gel, eluting with 50–60% EtOAc/pentane, to give epothilone B (4) (1.2 mg, 2.4 μmol, 78%) as a colorless oil: [α]D$^{23}$−36.7 (c 0.12, CHCl₃); $^1$H NMR (400 MHz, CDCl₃) δ 6.97 (s, 1H), 6.59 (s, 1H), 5.42 (dd, J=2.8, 7.9 Hz, 1H), 4.1–4.3 (m, 2H), 3.77 (bs, 1H), 3.2–3.35 (m, 1H), 2.81 (dd, J=4.5, 7.6 Hz, 1H), 2.69 (s, 3H), 2.66 (bs, 1H), 2.4–2.55 (m, 1H), 2.36 (dd, J=2.3, 13.6 Hz, 1H), 2.1–2.2 (m, 1H), 2.09 (s, 3H), 1.85–2.0 (m, 1H), 1.6–1.7 (m, 1H), 1.35–1.55 (m, 4H), 1.37 (s, 3H), 1.28 (s, 3H), 1.17 (d, J=6.8 Hz, 3H), 1.08 (s, 3H), 1.00 (d, J=7.1 Hz); $^{13}$C NMR (100.5 MHz, CDCl₃) δ 220.6, 170.5, 165.1, 151.8, 137.5, 119.7, 116.1, 74.1, 72.9, 61.6, 61.3, 53.1, 42.9, 39.2, 36.4, 32.3, 32.1, 30.8, 29.7, 22.7, 22.3, 21.4, 19.6, 19.1, 17.0, 15.8, 13.6; HRMS (CI) calculated for C₂₇H₄₂NO₅S (M+H$^+$) 492.2784, found 492.2775.

Example 24

This example describes the synthesis of alkyne 88 as illustrated in Scheme 4. To a stirred solution of potassium tert-butoxide (0.27 mL, 1.0 M THF solution) in THF (0.5 mL) at −78° C. was added a solution of (diazomethyl)phosphonate (40.2 mg, 1.25 mmol) in THF (0.5 mL). After 5 minutes a solution of 76 (110 mg, 0.21 mmol) in THF (0.5 mL ) was added dropwise, and the mixture was stirred at −78° C. for 12 hours. The mixture was then warmed to room temperature and was quenched with saturated aqueous NH₄Cl. The aqueous layer was extracted with 3×5 mL portions of Et₂O, and the combined organic extracts were dried (MgSO₄), concentrated in vacuo, and purified by chromatography (SiO₂, 5% Et₂O/hexane) to give 88 (85 mg, 80%) as colorless crystals: [α]D$^{24}$−24.1 (c 1.12, CHCl₃); mp 52–54° C.; IR (film) 3310 2951, 2927, 2883, 2854, 1743, 1691,1472,1254,1089, 990, 837, 775 cm$^{-1}$; $^1$H NMR (CDCl₃, 300 MHz) δ 4.45 (1H, dd, J=3.1, 7.5 Hz), 3.76 (1H dd, J=2.1, 6.4 Hz), 3.65 (1H, s), 3.33 (1H, qn, J=7.5) 2.40–2.26 (3H, m), 2.06 (1H, s), 1.24 (3H, s), 1.18 (3H, d, J=6.9 Hz), 1.17 (3H, 3H), 1.07 (3H, d, J=7.0 Hz), 0.92 (9H, s), 0.86 (9H, s), 0.08 (3H, s), 0.07 (3H, s), 0.00 (3H, s); $^{13}$C NMR (CDCl₃, 75 MHz) δ 218.6, 172.3, 85.6, 75.7, 73.3, 70.8, 53.9, 46.5, 32.1, 26.1, 23.7, 18.7, 18.5, 18.2, 15.8, −3.3, −3.9, −4.5, −4.7; HRMS (CI) calculated for C₂₇H₅₂Si₂O₅ (M+H$^+$) 512.3353, found 512.3342.

Example 25

This example describes the synthesis of enyne 90 as illustrated in Scheme 4. To a stirred solution of 88 (70.0 mg, 0.135 mmol) in Et₂O (1.0 mL) and DMF (0.4 mL) at room temperature was added Et₃N (18.8 μL, 0.135 mmol) and CuI (25.7 mg, 0.135 mmol). After the mixture turned clear (approximately 5 minutes), a solution of 56 (29.1 mg, 0.068 mmol) in Et₂O (1.0 mL) was added, and the mixture was stirred for 18 hours. The reaction mixture was quenched with saturated aqueous Na₂S₂O₃ (5 mL) and was extracted with Et₂O (3×2 mL). The combined organic extracts were dried (MgSO₄), concentrated in vacuo, and purified by flash chromatography over silica gel (50–60% CH₂Cl₂/hexanes) to give 90 (35.6 mg, 60%) as a colorless oil: [α]D$^{23}$−16.7 (c 1.01); IR (film) 2927, 2857, 2371, 2341, 1743, 1683, 1648, 1482, 1251, 991, 837 cm$^{-1}$; $^1$H NMR (CDCl₃, 300 MHz) δ 6.91(1H, s), 6.46 (1H, s), 5.36 (1H, t, J=4.7 Hz), 4.45 (1H, dd, J=3.1, 6.9), 4.11 (1H, t, J=6.6), 3.76–3.72 (1H, m), 3.74–3.67 (1H, m), 3.67 (3H, s), 3.36–3.31 (1H, qn, J=6.8), 2.71 (3H, s), 2.41–2.25 (7H, m), 2.01 (3H, s), 1.80 (3H, s), 1.24 (3H, s), 1.16 (3H, s), 1.12 (3H, d, J=7.0), 1.05 (3H, d, J=6.8), 0.92 (9H, s), 0.88 (9H, s), 0.87 (9H, s), 0.09 (3H, s), 0.06 (6H, s), 0.04 (3H, s), 0.01 (3H, s), –0.00 (3H, s); $^{13}$C NMR (CDCl$_3$, 75 MHz): δ 218.0, 172.4, 164.3, 153.2, 142.5, 132.2, 122.2, 118.6, 118.9, 83.1, 80.2, 78.6, 75.9, 73.5, 53.7, 51.6, 46.3, 40.4, 35.7, 32.6, 29.7, 29.2, 26.1, 26.0, 25.8, 23.8, 21.7, 19.2, 18.9, 18.4, 18.2, 16.2, 15.7, 13.9, –3.3, –3.9, –4.4, –4.6, –4.7, –4.9; HRMS (CI) calculated for C$_{46}$H$_{34}$O$_6$Si$_3$SN (M+H$^+$) 862.5327, found 862.5325.

Example 26

This example describes the synthesis of methyl ester 80 from compound 90 as illustrated in Scheme 4. A suspension of 90 (10 mg, 0.011 mmol) and Lindlar's catalyst (1.35 mg, 5% Pd) was stirred at room temperature under an atmosphere of H$_2$ for 28 hours. The suspension was filtered through silica gel (Et$_2$O rinse), concentrated in vacuo, and purified by flash chromatography over silica gel (40–60% CH$_2$Cl$_2$/hexane) to give 80 (6.8 mg, 68%) as colorless oil: [α]D$^{24}$+3.6 (c 1.00, CHCl$_3$); IR (film) 1743, 1699 cm$^{-1}$; $^1$H NMR (300 MHz, CDCl$_3$) δ 6.91 (1H, s), 6.45 (1H, s), 5.58 (1H, t, J=9.2 Hz), 5.2–5.35 (1H, m), 5.16 (1H, t, J=6.6 Hz), 4.39 (1H, dd, J=3.1, 6.9 Hz), 4.09 (1H, t, J=6.6 Hz), 3.8–3.9 (1H, m), 3.6–3.7 (1H, m); 3.66 (3H, s), 3.03 (1H, qn, J=6.7 Hz), 2.70 (3H, s), 2.65–2.75 (2H, m), 2.3–2.5 (2H, m), 2.15–2.35 (3H, m), 1.99 (3H, s), 1.64 (3H, s), 1.19 (3H, s), 1.06 (3H, s), 1.03 (3H, d, J=7.1 Hz), 1.00 (3H, d, J=7.0 Hz), 0.92 (9H, s), 0.88 (9H, s), 0.86 (9H, s), 0.08 (3H, s), 0.07 (6H, s), 0.04 (3H, s), 0.00 (3H, s), –0.01 (3H, s); $^{13}$C NMR (75 MHz, CDCl$_3$) δ 218.0, 172.6, 164.5, 153.4, 142.5, 135.5, 131.7, 128.7, 122.2, 119.0, 115.2, 79.1, 76.1, 74.2, 53.5, 51.8, 46.4, 40.4, 37.9, 35.6, 30.9, 26.4, 26.2, 26.0, 24.0, 23.9, 19.4, 19.3, 18.7, 18.4, 14.9, 14.1, –3.3, –3.7, –4.3, –4.4, –4.7; HRMS (CI) calculated for C$_{46}$H$_{86}$O$_6$Si$_3$SN (M+H$^+$) 864.5484, found 864.5510.

Example 27

This example describes the saponification of methyl ester 90 to form carboxylic acid 80 as illustrated in Scheme 4. To a stirred solution of the methyl ester (51 mg, 59 μmol) in i-PrOH (1 mL) was added NaOH (11.5 μL, 62 μmol, 5.4 M in H$_2$O ), and the mixture was heated at 45° C. in a sealed tube. After 16 hours, the solution was concentrated, diluted with aqueous HCl (20 mL, 0.5 M) and extracted with Et$_2$O (4×50 mL). The dried (Mg$_2$SO$_4$) extract was concentrated in vacuo and purified by chromatography over silica gel, eluting with 5–20% EtOAc/hexanes, to give acid 80 (33 mg, 34 μmol, 66%) as a colorless oil: IR (neat) 3500–2500, 1713 cm$^{-1}$; $^1$H NMR (300 MHz, CDCl$_3$) δ 6.93 (s, 1H), 6.67 (s, 1H), 5.52 (t, J=9.6 Hz, 1H), 5.3–5.4 (m, 1H), 5.23 (t, J=7.4 Hz, 1H), 4.41 (dd, J=3.3, 6.6 Hz, 1H), 3.75–3.85 (m, 1H), 2.9–3.1 (m, 2H), 2.71 (s, 3H), 2.5–2.8 (m, 2H), 2.1–2.6 (m, 4H), 1.9–2.1 (m, 1H), 1.93 (s, 3H), 1.71 (s, 3H), 1.16 (s, 3H), 1.13 (s, 3H), 1.04 (d, J=7.0 Hz, 3H), 9.94 (obscured d, 3H), 0.92 (s, 9H), 0.88 (18H, s), 0.12 (s, 6H), 0.09 (s, 3H), 0.06 (s, 3H), 0.03 (s, 3H), –0.01 (s, 3H); HRMS (CI) calculated for C$_{45}$H$_{84}$O$_6$Si$_3$SN (M+H$^+$) 850.5327, found 850.5281.

Example 28

This example describes the deprotection of carboxylic acid 80 to form triene 82 as illustrated in Scheme 4. To a stirred solution of carboxylic acid 80 (154 mg, 181 μmol) in THF (3.9 mL) at 0° C. was added TBAF (1.1 mL, 1.1 mmol, 1 M in THF). The solution was allowed to warm slowly to room temperature overnight. After 16 hours, the mixture was diluted with EtOAc, washed with saturated aqueous NH$_4$Cl (50 mL), and extracted with EtOAc (4×100 mL). The dried (Mg$_2$SO$_4$) extract was concentrated in vacuo and purified by chromatography over silica gel, eluting with 2–5% MeOH/CH$_2$Cl$_2$, to give 82 (118.5 mg, 160 μmol, 89%) as a white foam: [α]D$^{23}$–2.6 (c 3.50, CHCl$_3$); IR (neat) 3500–2500, 1709 cm$^{-1}$; $^1$H NMR (300 MHz, CDCl$_3$) δ 6.95 (s, 1H), 6.70 (s, 1H), 5.56 (t, J=10.0 Hz, 1H), 5.3–5.45 (m, 1H), 5.24 (t, J =7.3 Hz, 1H), 4.35–4.45 (m, 1H), 4.16 (t, J=6.2 Hz, 1H), 3.75–3.85 (m, 1H), 3.03 (m, 2H), 2.75–2.85 (m, 1H), 2.72 (s, 3H), 2.65–2.75 (m, 1H), 2.2–2.7 (m, 5H), 1.99 (s, 3H), 1.74 (s, 3H), 1.15 (s, 3H), 1.14 (s, 3H), 1.04 (d, J=7.1 Hz, 3H), 0.98 (d, J=6.9 Hz, 3H), 0.92 (s, 9H), 0.87 (s, 9H), 0.12 (s, 3H), 0.10 (s, 3H), 0.07 (s, 3H), 0.06 (s, 3H); $^{13}$C NMR (75 MHz, CDCl$_3$) δ218.1, 176.0, 165.1, 152.4, 141.9, 137.5, 131.6, 127.8, 120.8, 118.8, 115.1, 77.2, 76.0, 73.5, 53.6, 46.3, 40.1, 38.0, 34.1, 30.8, 26.2, 26.0, 23.7, 23.5, 19.0, 18.9, 18.7, 18.5, 18.1, 15.0, 14.6, –3.6, –4.1, –4.2, –4.6; HRMS (CI) calculated C$_{39}$H$_{70}$O$_6$Si$_2$SN (M+H$^+$) 736.4462, found 736.4451.

Example 29

This example describes the synthesis of compound 94. To a stirred solution of 92 (195 mg, 0.32 mmol) in THF (1.5 mL) was added 2-(trimethylsilyl)ethanol (69 μL, 0.48 mmol) and triphenylphosphine (56.8 mg, 0.80 mmol). The solution was cooled to 0° C. and diethyl azodicarboxylate was added. After 1.5 hours, the reaction was quenched with saturated aqueous NH$_4$Cl, and the solution was extracted with Et$_2$O. The extract was concentrated in vacuo, and the residue was purified by chromatography on silica gel, eluting with 5–10% Et2O/petroleum ether, to give 94 (175 mg, 75% ) as a colorless oil: [α]D$^{23}$–27.0 (c 1.03, CHCl$_3$; IR (neat) 1741, 1690 cm$^{-1}$; $^1$H NMR (300 MHz, CDCl$_3$) δ 7.23 (d, J=8.4 Hz, 2H), 6.85 (d, J=8.4 Hz, 2H), 4.39 (s, 2H), 4.3–4.4 (m, 1H), 3.83 (d, J=7.8 Hz, 1H), 3.80 (s, 3H), 3.58 (dd, J=5.7, 9.1 Hz, 1H), 3.31 (dq, J=7.2, 7.2 Hz, 1H), 3.18 (dd, J=7.3, 9.1 Hz, 1H), 2.46 (dd, J=3.1, 16.1 Hz, 1H), 2.26 (dd, J=7.0, 16.1 Hz, 1H), 1.7–1.85 (m, 1H), 1.14 (s, 3H), 1.06 (s, 3H), 101 (d, J=6.9 Hz, 3H), 0.95 (d, J=6.9 Hz, 3H), 0.88 (s, 9H,), 0.87 (s, 9H), 0.08 (s, 3H), 0.05 (s, 6H), 0.02 (s, 3H); $^{13}$C NMR (CDCl$_3$) δ 218.5, 172.7, 159.3, 131.0, 129.5, 113.9, 74.1, 73.1, 71.8, 55.5, 53.6, 51.8, 46.3, 40.4, 38.9, 29.9, 26.5, 26.2, 24.0, 18.8, 18.7, 18.4, 17.0, 15.7, –3.3, –3.5, –4.3, –4.4; HRMS (CI) calcd. for C$_{38}$H$_{73}$O$_7$Si (M+H$^+$) 725.4664, found 725.4666.

Example 30

This example describes the synthesis of compound 95. To a stirred solution of 94 (150 mg, 0.20 mmol) in EtOH (4.0 mL) was added palladium-on-carbon (55 mg, 10% Pd), and the mixture was stirred under an atmosphere of H$_2$. After 1 hours, the H$_2$ atmosphere was replaced by Ar, and the mixture was filtered through Celite (EtOH rinse). The filtrate was concentrated in vacuo, and the residue was purified by chromatography on silica gel, eluting with 10–30% Et2O/petroleum ether, to give 95 (108 mg, 89%) as a colorless oil: [α]D$^{23}$–8.47 (c 1.18, CHCl$_3$); IR (neat) 3538, 1743, 1694 cm$^{-1}$; $^1$H NMR (300 MHz, CDCl$_3$) δ 4.40 (dd, J=2.9, 6.9 Hz, 1H), 4.17–4.11 (m, 2H) 3.93 (dd, J=2.0, 7.8 Hz, 1H), 3.6–3.7 (m, 1H), 3.5–3.6 (m, 1H), 3.31 (dq, J=7.5, 7.5 Hz, 1H), 2.43 (dd, J=2.7, 16.3 Hz, 1H), 2.26 (1H, dd, J=6.9, 16.3 Hz), 1.55–1.65 (1H, m), 1.22 (3H, s), 1.13 (3H, s), 1.09 (d, J=7.0 Hz, 3H), 0.95 (d, J=7.1 Hz, 3H), 0.92 (s, 9H), 0.87 (s, 9H), 0.85 (m, 2H), 0.02 (s, 9H) 0.12 (s, 3H), 0.10 (s, 3H), 0.09 (s, 3H), 0.01 (s, 3H); $^{13}$C NMR (CDCl$_3$) δ 218.4, 172.8, 78.2, 73.6, 64.9, 60.3, 53.9, 51.9, 47.0, 40.3, 39.8, 29.9, 26.4, 26.2, 24.1, 19.1, 18.6, 18.4, 17.2 16.1, –3.0, –3.4, –3.6, –4.3, –4.4.

Example 31

This example describes the synthesis of compound 96. To a stirred mixture of 95 (200 mg, 0.33 mmol) and powdered molecular sieves (300 mg) in $CH_2Cl_2$ (6.0 mL) was added sequentially N-methylmorpholine-N-oxide (97 mg, 0.83 mmol) followed by tetra-n-propylammonium perruthenate (11.6 mg, 33 μmol). After 1.5 hours, the mixture was filtered through silica ($Et_2O$ rinse), and the filtrate was concentrated in vacuo to give the crude aldehyde as a colorless oil.

To a stirred solution of the crude aldehyde and $K_2CO_3$ (91 mg, 0.66 mmol) in MeOH (5.0 mL) was added dimethyl 1-diazo-2-oxopropylphosphonate (74 mg, 0.46 mmol). The solution was stirred for 4 hours at room temperature, diluted with $Et_2O$ (30 mL), washed with aqueous $NaHCO_3$ (5%), and extracted with $Et_2O$ (3×30 mL). The dried ($Mg_2SO_4$) extract was concentrated in vacuo, and the residue was purified by flash chromatography on silica gel, eluting with 2% $Et_2O$/hexanes, to give 96 (155 mg, 78%) as a colorless oil: $[\alpha]D^{23}$-25.1 (c 2.50, $CHCl_3$); IR (neat) 2946, 2928, 2848, 1734, 1690, 1468; $^1H$ NMR (300 MHz, $CDCl_3$) δ 4.45 (dd, J=3.1, 7.5 Hz, 1H), 4.11–4.16 (m, 2H), 3.76 (dd, J=2.1, 6.4 Hz, 1H), 3.35 (dq, J=7.3, 7.3 Hz, 1H), 2.22–2.24 (m, 3H), 2.06 (s, 1H),1.25 (s, 3H), 1.18 (d, J=7.5 Hz, 3H), 1.17 (s, 3H), 1.07 (d, J=6.8 Hz, 3H), 0.95 (obscured m, 2H) 0.92 (s, 9H), 0.86 (s, 9H), 0.10 (s, 3H), 0.07 (s, 3H), 0.07 (s, 3H), 0.03 (s, 9H), 0.02 (s, 3H); $^{13}C$ NMR (75 MHz, $CDCl_3$) δ 218.6, 172.1, 85.6, 75.7, 73.3, 70.8, 62.7, 53.8, 46.5, 40.6, 32.2, 26.1, 26.0, 18.7, 18.5, 18.2, 17.2, 15.9, –1.6, –3.3, –3.9, –4.4, –4.7; HRMS (FAB) calcd. for $C_{51}H_{63}O_5Si_3$ (M+H$^+$) 599.3983, found 599.3982

Example 32

This example describes the synthesis of compound 98. To a stirred solution of 96(60.0 mg, 0.10 mmol) and bis(triphenylphosphine)palladium dichloride (1.4 mg, (0.002 mmol) in THF (0.5 mL) at room temperature was added slowly tri-n-butyltin hydride (32.3 μL, 0.12 mmol). After 10 minutes, the solution was concentrated in vacuo, and the residue was purified by chromatography on silica gel, eluting with 5% $Et_2O$/hexanes, to give 98 (79 mg, 89%) as a colorless oil: $[\alpha]D^{23}$-9.6 (c 1.35, $CHCl_3$); IR (neat) 2955, 2928, 2856, 1736, 1472 cm$^{-1}$; $^1H$ NMR (300 MHz, $CDCl_3$) δ 6.12 (dd, J=7.5, 19.3 Hz, 1H), 5.89 (d, J=19.3 Hz, 1H), 4.43 (dd, J=3.2, 6.8 Hz, 1H), 4.15 (m, 2H), 3.85 (dd, J=1.5, 7.9 Hz, 1H), 3.07 (dq, J=7.1, 7.1 Hz, 1H), 2.40 (dd, J=3.2, 16.2 Hz, 1H), 2.23 (dd, J=6.8, 16.2 Hz, 1H), 1.45–1.53 (m, 6H), 1.23–1.37 (m, 12H), 1.19 (s, 3H), 1.09 (s, 3H), 1.03 (d, J=7.0, 3H), 1.03 (d, J=6.9, 3H), 0.93 (s, 9H), 0.87 (s, 9H), 0.85–0.93 (m, 12H), 0.10 (s, 3H), 0.09 (s, 3H), 0.08 (s, 3H), 0.04 (s, 9H), 0.03 (s, 3H); $^{13}C$ NMR (100 MHz, $CDCl_3$) δ 218.8, 172.6, 150.7, 129.1, 74.0, 63.1, 53.9,47.5, 47.1,41.0, 29.6, 27.7, 26.6, 26.4, 24.5, 19.2, 18.9, 17.7, 15.9, 14.1, 9.9, –1.1, –2.9, –3.4, –4.0, –4.3.

Example 33

This example describes the synthesis of compound 102. To a stirred solution of 100 (1.00 g, 2.48 mmol) in $CH_2Cl_2$ (25 mL) at –78° C. was added 2,6-lutidine (61 mg, 0.66 mL, 5.72 mmol). After 4 minutes, triethylsilyl triflate (1.19 g, 1.0 mL, 4.5 mmol) was added to the cold solution, and after 30 minutes the reaction was quenched with saturated aqueous $NH_4Cl$ (60 mL) and extracted with Et2O (3×100 mL). The dried ($Mg_2SO_4$) extract was concentrated in vacuo and the residue was purified by chromatography on silica gel, eluting with 30–50% Et2O/hexane, to give 102 (1.00 g, 78%) as a colorless oil: $[\alpha]D^{23}$+31.2 (c 1.63, $CHCl_3$); IR (neat) 1782, 1714 cm$^{-1}$; $^1H$ NMR (300 MHz, $CDCl_3$) δ 7.15–7.4 (m, 5H), 5.35–5.5 (m, 2H), 4.55–4.7 (m, 2H), 4.05–4.2 (m, 2H), 4.0–4.15 (m, 2H), 3.8–3.9 (m, 1H of a diastereomer), 3.4–3.5 (m, 1H of a diastereomer), 3.36 (d, J=13.1 Hz, 1H of a diastereomer), 2.7–2.8 (m, 1H of a diastereomer), 2.45–2.55 (m, 2H), 2.46 (q, J=7.3 Hz, 1H), 1.5–1.8 (m, 9H), 0.97 (t, J=7.8 Hz, 9H), 0.62 (q, J=7.6Hz, 6H); $^{13}C$ NMR (75 MHz, $CDCl_3$) δ 173.9, 173.7, 153.3, 135.5, 134.9, 129.6, 129.1, 127.5, 124.0, 97.6, 96.9, 71.1, 66.7, 65.5, 65.2, 62.3, 61.9, 55.8, 37.9, 34.2, 33.7, 30.8, 30.7, 26.0, 25.7, 22.0, 21.9, 19.7, 19.4, 18.5, 6.7, 5.1; HRMS (CI) calcd. for $C_{28}H_{44}NO_6Si$ (M+H$^+$) 518.2938, found 518.2908.

Example 34

This example describes the synthesis of compound 104 To a stirred solution of ethanethiol (361 mg, 430 μL, 5.82 mmol) in THF (25 mL) at room temperature was added KH (55 mg, 0.48 mmol, 35% in mineral oil). After 30 minutes, the mixture was cooled to 0° C. and a solution of 102 (1.00 g, 1.94 mmol) in THF (10 mL) was added via cannula during 5 minutes. An additional amount of THF (5 mL) was added, and after 1 hour at room temperature the reaction was quenched with saturated aqueous $NH_4Cl$ (25 mL). Air was passed through the solution for 2 hours to remove excess ethanethiol, and the mixture was extracted with $Et_2O$ (3×100 mL). The dried ($Mg_2SO_4$) extract was concentrated in vacuo and the residue was taken up in 10% $Et_2O$/petroleum ether, from which 4-benzyloxazolidin-2-one crystallized as a colorless solid. The decanted solution was concentrated and the residue was purified by chromatography on silica gel, eluting with 30% $Et_2O$/hexane, to give the thioester (730 mg, 97%) as a colorless oil: $[\alpha]D^{23}$–16.8 (c 2.73, $CHCl_3$); IR (neat) 1684 cm$^{-1}$; $^1H$ NMR (300 MHz, $CDCl_3$) δ 5.35–5.5 (m, 1H), 4.55 (bs, 1H), 3.9–4.2 (m, 3H), 3.8–3.9 (m, 1H), 3.45–3.6 (m, 1H), 3.36 (d, J=13.1 Hz, 1H), 2.75–2.9 (m, 2H), 2.4–2.6 (m, 2H), 1.4–1.9 (m, 6H), 1.21 (t, J=7.5 Hz, 3H), 0.97 (t, J=7.8 Hz, 9H), 0.62 (q, J=7.8 Hz, 6H); $^{13}C$ NMR (75 MHz, $CDCl_3$) δ 205.1, 205.0, 135.24, 135.16, 97.9, 97.4, 78.6, 65.7, 65.5, 62.3, 62.2, 34.5, 30.8, 25.9, 25.7, 22.6, 22.1, 22.0, 19.7, 19.6, 18.4, 14.8, 6.7, 5.1; HRMS (CI) calcd. for $C_{20}H_{37}NO_4SSi$ (M+H$^+$) 401.2182, found 401.2172

To a stirred solution of CuI (2.60 g, 13.67 mmol) in $Et_2O$ (120 mL) at 0° C. was added MeLi (17.8 mL, 24.9 mmol, 1.4M in $Et_2O$). The mixture was cooled to –50° C. and a solution of the thioester (960 mg, 2.49 mmol) in $Et_2O$ (50 mL) was added via cannula. An additional amount of $Et_2O$ (5 mL) was added to rinse the flask. After 30 minutes, the reaction was quenched with saturated aqueous $NH_4Cl$ (200 mL), and the mixture was extracted with $Et_2O$ (3×120 mL). The dried ($Mg_2SO_4$) extract was concentrated in vacuo and the residue was purified by chromatography on silica gel, eluting with 15% $Et_2O$/hexane, to givethe methyl ketone (548 mg, 62%) as a colorless oil: $[\alpha]D^{23}$–11.0 (c 3.26, $CHCl_3$); IR (neat) 1719 cm$^{-1}$; $^1H$ NMR (300 MHz, $CDCl_3$) δ 5.35–5.5 (m, 5H), 4.5–4.55 (m, 1H), 3.9–4.1 (m, 3H), 3.75–3.9 (m, 1H), 3.4–3.5 (m, 1H), 2.3–2.5 (m, 2H), 2.10 (s, 3H) 1.4–1.9 (m, 6H), 0.97 (t, J=7.8 Hz, 9H), 0.62 (q, J=7.8 Hz, 6H); $^{13}C$ NMR (75 MHz, $CDCl_3$) δ 211.7, 135.2, 135.1, 123.8, 123.5, 97.7, 97.3, 79.0, 65.5, 65.2, 62.2, 62.1, 33.2, 30.7, 25.8, 25.6, 25.5, 22.0, 19.6, 19.5, 18.2, 6.7, 5.1; HRMS (CI) calcd. for $C_{19}H_{37}O_4Si$ (M+H$^+$) 357.2461, found 357.2455.

To a stirred solution of 53 (1.26 g, 5.08 mmol) in THF (9 mL) at –78° C. was added n-BuLi (4.7 mL, 5.00 mmol, 1.2 M in hexanes), and after 20 minutes, a solution of the methyl ketone (520 mg, 1.45 mmol) in THF (6 mL) was added via cannula. An additional amount of THF (2 mL) was added to rinse the flask. After 30 minutes, the solution was allowed to warm slowly to room temperature during 1 hour, then was cooled at –78° C. for an additional 30 minutes before the reaction was quenched with saturated aqueous $NH_4Cl$ (50 mL). The mixture was extracted with $Et_2O$ (3×65 mL), and the dried ($Mg_2SO_4$) extract was concentrated in vacuo. The residue was purified by chromatography on silica gel, eluting with 20% $Et_2O$/hexanes, to give the thiazole (627 mg, 96%) as a colorless oil: [α]$_D^{23}$ −33.9 (c 2.56, CHCl$_3$); IR (neat) 2950, 1512, 1455 cm$^{-1}$; $^1$H NMR (300 MHz, CDCl$_3$) δ 6.91 (s, 1H), 6.45, (s, 1H), 5.35–5.5 (m, 1H), 4.5–4.6 (m, 1H), 3.9–4.2 (m, 3H), 3.8–3.9 (m, 1H), 3.45–3.6 (m, 1H), 2.70 (s, 3H), 2.2–2.4 (m, 2H), 1.99 (d, J=1.0 Hz, 3H), 1.4–1.9 (m, 6H), 0.92 (t, J=7.9 Hz, 9H), 0.72 (q, J=7.9 Hz, 6H); $^{13}$C NMR (75 MHz, CDCl$_3$,) δ 164.2, 153.1, 142.5, 142.2, 133.4, 125.6, 125.5, 118.7, 118.6, 114.9, 97.4, 97.2, 78.4, 77.3, 65.4, 65.3, 62.0, 61.9, 35.0, 34.9, 30.6, 25.4, 21.7, 19.4, 19.4, 19.1, 13.8, 6.7, 4.7; HRMS (CI) calcd. for C$_{24}$H$_{42}$NO$_3$SSi (M+H$^+$) 452.2655, found 452.2645.

To a stirred solution of freshly prepared MgBr$_2$(631 mg, 26.2 mmol of Mg, and 2.38 mL, 27.7 mmol, of 1,2-dibromoethane) in Et$_2$O (50 mL) at room temperature was added the thiazole (556 mg, 1.20 mmol) in Et$_2$O (5 mL) followed by saturated aqueous NH$_4$Cl (approx 50 μL). After 3.5 hours, the mixture was cooled to 0° C. and carefully quenched with saturated aqueous NH4Cl (50 mL). The mixture was extracted with Et$_2$O (3×100 mL), and the dried (Mg$_2$SO$_4$) extract was concentrated in vacuo. The residue was purified by chromatography on silica gel, eluting with 30% Et$_2$O/hexanes, to give 104 (390 mg, 89%) as a colorless oil: [α]$_D^{23}$ −31.0 (c 2.74); IR (neat) 3374 cm$^1$; $^1$H NMR (300 MHz, CDCl$_3$) δ 6.92 (s, 1H), 6.44, (s, 1H), 5.31 (t, J=7.7 Hz, 1H), 4.14 (d, J=12.2 Hz, 1H), 4.1–4.2 (m, 1H), 4.00 (d, J=12.2 Hz, 1H), 2.71 (s, 3H), 2.4–2.5 (m, 1H), 2.2–2.3 (m, 2H), 2.00 (s, 3H), 1.80 (s, 3H), 0.92 (t, J=7.9 Hz, 9H), 0.72 (q, J=7.9 Hz, 6H); $^{13}$C NMR (75 MHz, CDCl$_3$) δ 164.8, 153.0, 142.4, 137.7, 124.4, 119.0, 115.4, 78.4, 62.0, 61.9, 35.5, 29.9, 26.0, 22.2, 19.3, 18.5, 14.3, 6.7, 4.7; HRMS (CI) calcd. for C$_{19}$H$_{34}$NO$_2$SSi (M+H$^+$) 368.2080, found 368.2061.

Example 35

This example describes the synthesis of compound 106. To a stirred solution of 104 (35 mg, 95 μmol) in CH$_2$Cl$_2$ (0.6 mL) at 0° C. was added Et$_3$N (23 μL, 161 μmol) followed by methanesulfonic anhydride (21 mg, 119 μmol). After 10 minutes, acetone (0.6 mL) was added followed by LiCl (40 mg, 950 μmol). After 4 hours at room temperature, the solution was concentrated in vacuo to remove acetone, diluted with saturated aqueous NH$_4$Cl, and extracted with Et$_2$O. The dried (Mg$_2$SO$_4$) extract was concentrated in vacuo and the residue was purified by chromatography on silica gel, eluting with 10–20% Et$_2$O/petroleum ether, to give 106 (36 mg, 97%) as a colorless oil: [α]$_D^{23}$ +28.1 (c 1.11, CHCl$_3$); IR (neat) 2954, 2875, 1453,1072 cm$^{-1}$; $^1$H NMR (300 MHz, CDCl$_3$) δ 6.94 (s, 1H), 6.49 (s, 1H), 5.41 (dt, J=1.3, 7.5 Hz, 1H), 4.15 (m, 1H), 4.14 (d, J=10.8, 1H), 4.00 (d, J=10.8, 1H), 2.71 (s, 3H), 2.35 (m, 2H), 2.01 (d, J=1.2, 3H), 1.75 (d, J=1.2, 3H), 0.93 (t, J=7.69, 9H), 0.58 (q, J=7.39, 6H); $^{13}$C NMR (75 MHz, CDCl$_{13}$) δ 164.5, 153.5, 142.3, 133.4, 127.8, 119.4, 115.6, 78.4, 44.2, 35.8, 22.1, 19.6, 14.4, 7.2, 5.2; HRMS (FAB) calcd. for C$_{19}$H$_{33}$ClNOSSi (M+H$^+$) 386.1741, found 386.1737.

Example 36

This example describes the synthesis of a compound C$_{50}$H$_{96}$NO$_6$SSi$_4$. A solution of 106 (44 mg, 114 μmol), tris(dibenzylideneactone)dipalladium-chloroform (7.1 mg, 6.8 μmol) and triphenylarsine (8.4 mg, 27 μmol) in THF (0.4 mL) was stirred at room temperature for 10 minutes. A solution of 98 (107 mg, 120 μmol) in THF (1.0 mL) was added, and the flask was briefly opened to the atmosphere, resealed, and heated to 65° C. After 18 hours, the mixture was concentrated in vacuo and the residue was purified by chromatography on silica gel, eluting with 5% Et$_2$O/hexanes, to give (82 mg, 76%) a colorless oil: [α]$_D^{23}$ −6.2 (c 1.23, CHCl$_3$); IR (neat) 2955, 2856, 1753, 1694, 1471 cm$^{-1}$; $^1$H NMR (300 MHz, CDCl$_3$) δ 6.91(s, 1H), 6.47 (s, 1H), 5.52 (dd, J=7.9, 15.6 Hz, 1H), 5.32 (dt, J=6.7, 8.5 Hz, 1H), 5.17 (t, J=7.3, 1H), 4.40 (dd, J=3.1, 6.7 Hz, 1H), 4.15–4.18 (m, 2H), 3.82 (dd, J=1.8, 7.2, 1H), 3.02 (dq, J=7.1, 7.1 Hz, 1H), 2.72 (s, 3H), 2.66 (d, J=6.6 Hz, 2H), 2.20–2.44 (m, 3H), 2.00 (s, 3H), 1.26 (s, 3H), 1.07 (s, 3H), 1.01 (d, J=7.0 Hz, 3H), 1.00 (d, J=6.0 Hz, 3H), 0.93 (t, J=7.8 Hz, 9H), 0.91 (s, 9H), 0.87 (s, 9H), 0.58 (q, J=7.8 Hz, 6H), 0.10 (s, 3H), 0.06 (s, 3H), 0.03 (s, 3H), 0.03 (s, 9H), 0.02 (s, 3H); $^{13}$C NMR (75 MHz, CDCl$_3$) δ 218.5, 172.6, 164.7, 153.6, 143.0, 136.0, 133.1, 129.7, 121.9, 119.0, 115.3, 79.0, 76.8, 63.1, 53.8, 46.6, 43.8, 42.8, 40.9, 26.6, 26.4, 19.6, 18.9, 18.6, 17.7, 16.7, 14.4, 7.3, 5.5, −1.1, −3.1, −3.4, −4.0, −4.2; HRMS (FAB) calcd. for C$_{50}$H$_{96}$NO$_6$SSi$_4$ (M+H$^+$) 950.6036, found 950.6065.

Example 37

This example describes the synthesis of a compound C$_{39}$H$_{70}$NO$_6$SSi$_2$. To a stirred solution of a compound made according to Example 36 (20 mg, 21 μmol) and powdered molecular sieves (100 mg) in THF (8.0 mL) at 0° C. was added tetra-n-butylammonium fluoride (16.5 mg, 63 μmol). After 6 hours, the mixture was filtered through glass wool, and aqueous citric acid (pH 5, 8 mL) was added to the filtrate, which was extracted with Et$_2$O. The dried (Mg$_2$SO$_4$) extract was concentrated in vacuo and the residue was purified by flash chromatography on silica gel, eluting with 4% MeOH/CH$_2$Cl$_2$, to give (12.8 mg, 83%) as a colorless oil: [α]$_D^{23}$ −22.4 (c 2.15, CHCl$_3$); IR (neat) 3252, 2956, 2929, 2856, 1712 cm$^{-1}$; $^1$H NMR (300 MHz, CDCl$_3$) δ 6.96 (s, 1H), 6.58, (s, 1H), 5.54 (dd, J=7.5, 15.2 Hz, 1H), 5.38 (dt, J=6.7, 15.2 Hz, 1H), 5.20 (t, J=7.8 Hz, 1H), 4.40 (dd, J=3.2, 6.4 Hz, 1H), 4.16–4.24 (m, 1H), 3.83–3.86 (m, 1H), 3.02–3.09 (m, 1H), 2.72 (s, 3H), 2.69–2.72 (m, 2H), 2.28–2.55 (m, 5H), 1.98–2.08 (m, 2H), 2.03 (s, 3H), 1.63 (s, 3H), 1.17 (s, 3H), 1.12 (s, 3H), 1.04 (d, J=6.9 Hz, 3H), 0.97 (d, J=6.9 Hz, 3H), 0.92 (s, 9H), 0.89 (s, 9H), 0.11 (s, 3H), 0.07 (s, 3H), 0.07 (s, 3H), 0.06 (s, 3H)); $^{13}$C NMR (75 MHz, CDCl$_3$) δ 218.8, 175.9, 165.4, 153.0, 142.1, 138.2, 133.3, 129.5, 120.6, 119.4, 115.7, 76.9, 76.7, 73.7, 54.0, 46.8, 43.6, 42.8, 40.4, 34.6, 30.1, 26.6, 26.4, 24.2, 20.1, 19.3, 18.9, 18.6, 16.9, 14.7, −3.1, −3.5, −3.7, −4.2; HRMS (FAB) calcd. for C$_{39}$H$_{70}$NO$_6$SSi$_2$ (M+H$^+$) 736.4462, found 736.4466.

Example 38

This example describes the synthesis of a compound C$_{39}$H$_{68}$NO$_5$SSi$_2$. To a stirred solution of a compound made according to Example 37 (22.0 mg, 30.0 μmol) in THF (0.5 mL) at 0° C. was added Et$_3$N (7.6 μL, 54 μmol) followed by 2,4,6-trichlorobenzoyl chloride (5.6 μL, 36 μmol). After 45 minutes, the mixture was diluted with THF (0.4 mL) and toluene (0.7 mL), and was added via syringe pump to a stirred solution of DMAP (6.5 mg, 53 μmol) in toluene (7.2 mL) at 75° C. during 3.5 h. After an additional 1 hour, the solution was allowed to cool to room temperature, diluted with EtOAc, washed with saturated aqueous NH$_4$Cl (20 mL), and extracted with EtOAc (4×40 mL). The dried (Mg$_2$SO$_4$) extract was concentrated in vacuo and the residue was purified by chromatography on silica gel, eluting with 5% EtOAc/hexanes, to give (19.4 mg, 71%) as a colorless oil: [α]$_D^{23}$ −2.12 (c 1.13, CHCl$_3$); IR (neat) 2929, 2856, 1735, 1700 cm$^{-1}$; $^1$H NMR (300 MHz, CDCl$_3$) δ 6.94 (s, 3H), 6.54 (s, 3H), 5.44–5.46 (m, 2H), 5.28 (m, 1H), 5.22 (dd, J=3.3, 9.7, 1H), 4.63 (dd, J=3.2, 8.7, 1H), 3.90 (m, 1H), 3.16 (dq, J=6.8, 6.8 Hz, 1H), 2.71 (s, 3H), 2.20–2.71 (m, 6H), 2.14 (s, 3H), 1.68 (s, 3H), 1.10 (d, J=6.8 Hz, 3H), 1.10 (s, 3H), 1.07 (s, 3H), 1.04 (d, J=7.0, 1H), 0.93 (s, 9H), 0.85 (s, 9H), 0.11 (s, 3H), 0.11 (s, 3H), 0.10 (s, 3H), 0.88 (s, 3H); $^{13}$C NMR (100 MHz, CDCl$_3$) δ 215.9, 170.7, 165.1, 153.1, 138.7, 137.8, 133.9, 128.3, 120.3, 119.8, 116.8, 80.8, 77.7, 73.3, 55.1, 44.1, 43.1, 42.3, 42.0, 32.8, 26.6, 26.4, 21.2, 19.7, 19.1, 18.9, 18.2, 18.0, 17.2, 15.2, −2.5, −3.4, −3.8, −3.8; HRMS (FAB) calcd. for $C_{39}H_{68}NO_5SSi_2$ (M+H$^+$) 718.4357, found 718.4345.

Example 39

This example describes the synthesis of a compound $C_{27}H_{40}NO_3S$. To a stirred solution of a compound made according to Example 38 (14.5 mg, 20 μmol) in $CH_2Cl_2$ (125 μL) at 0° C. was added trifluoroacetic acid (112 μL). After 8 hours, the mixture was concentrated in vacuo, and the residue was purified by chromatography on silica gel, eluting with 20–50% EtOAc/hexanes, to give (9.3 mg, 19 μmol, 95%) as a colorless waxy solid: $[\alpha]D^{23}$−35.4 (c 0.50, CHCl$_3$); IR (neat) 2971, 2927, 1729, 1691 cm$^{-1}$; $^1$H NMR (300 MHz, CDCl$_3$) δ 6.98 (s, 1H), 6.55 (s, 1H), 5.53–5.48 (m, 2H), 5.38 (dd, J=2.8, 9.4 Hz, 1H), 5.23 (m, 1H), 4.23 (dd, J=4.3, 8.2 Hz, 1H), 3.71 (m, 1H), 3.27 (dq, J=5.8, 6.7 Hz, 1H), 2.27–2.77 (m, 6H), 2.72 (s, 3H), 2.11 (s, 3H), 1.69 (s, 3H), 1.26 (s, 3H), 1.17 (d, J=6.8 Hz, 3H), 1.10 (d, J=7.0 Hz, 3H), 1.05 (s, 3H); $^{13}$C NMR (75 MHz, CDCl$_3$) δ 219.7, 171.0, 165.2, 152.7, 138.4, 137.8, 132.8, 129.6, 120.4, 120.2, 116.6, 79.2, 77.0, 76.4, 74.6, 72.3, 53.3, 44.7, 42.9, 40.3, 39.5, 32.6, 21.6, 20.0, 19.6, 17.8, 17.1, 15.9, 15.2; HRMS (FAB) calcd. for $C_{27}H_{40}NO_3S$ (M+H$^+$) 490.2627, found 490.2634.

The present invention has been described in accordance with working embodiments; however, it will be understood that certain modifications may be made thereto without departing from the invention. We claim as our invention the preferred embodiment and all such modifications and equivalents as come within the true spirit and scope of the following claims.

We claim:

1. A compound according to the formula:

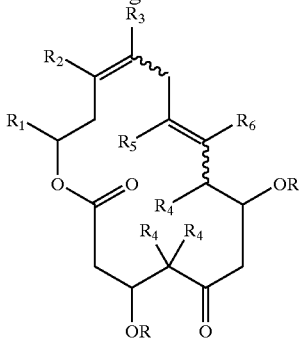

where R substituents independently are H, lower alkyl, or a protecting group, $R_1$ is

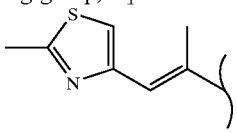

$R_2$ and $R_3$ independently are H or lower aliphatic groups, $R_4$ substituents independently are selected from the group consisting of lower aliphatic groups, and $R_5$ and $R_6$ independently are H or lower aliphatic.

2. The compound according to claim 1 having the formula

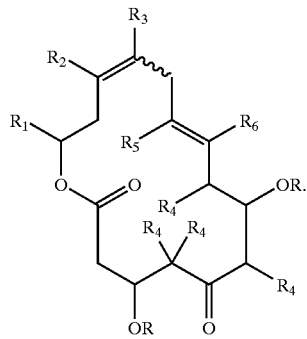

3. The compound according to claim 1 having the formula

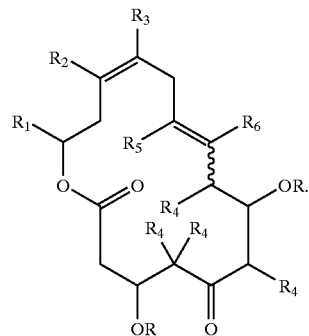

4. The compound according to claim 1 having the formula

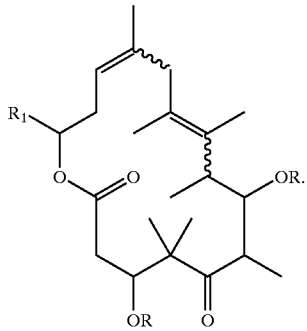

* * * * *

UNITED STATES PATENT AND TRADEMARK OFFICE
CERTIFICATE OF CORRECTION

| | | |
|---|---|---|
| PATENT NO. | : 6,958,401 B2 | Page 1 of 1 |
| APPLICATION NO. | : 10/352340 | |
| DATED | : October 25, 2005 | |
| INVENTOR(S) | : White et al. | |

It is certified that error appears in the above-identified patent and that said Letters Patent is hereby corrected as shown below:

In the Claims:

Claim 1, page 43, lines 33-45, the formula:

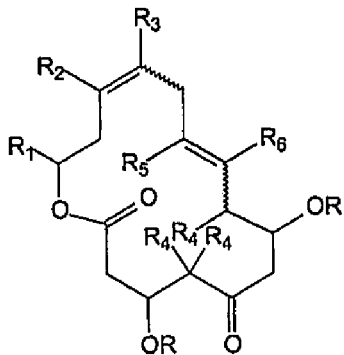

should read:

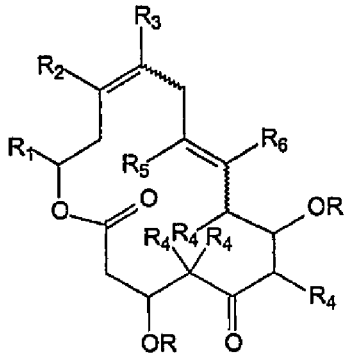

Signed and Sealed this

Eighteenth Day of September, 2007

JON W. DUDAS
*Director of the United States Patent and Trademark Office*